(12) United States Patent
Sollogoub et al.

(10) Patent No.: US 10,947,323 B2
(45) Date of Patent: Mar. 16, 2021

(54) CAPPED CYCLODEXTRIN-HYDROPHOBIC MOIETY CONJUGATE, CYCLODEXTRIN SUPRAMOLECULAR POLYMER, AND CYCLODEXTRIN-SIRNA COMPLEX AND METHOD OF SYNTHESIS THEREOF

(71) Applicants: SORBONNE UNIVERSITE, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); ASSISTANCE PUBLIQUE—HOPITAUX DE PARIS, Paris (FR); UNIVERSITÉ DE PARIS, Paris (FR)

(72) Inventors: Matthieu Sollogoub, Paris (FR); Vincent Calvez, Paris (FR); Anne-Geneviève Marcelin, Paris (FR); Laurent Bouteiller, Bourg la Reine (FR); Mickaël Menand, Alfortville (FR); Pierre Evenou, Paris (FR); Adélie Gothland, Paris (FR); Dmitri Colesnic, Paris (FR); Julien Rossignol, Paris (FR)

(73) Assignees: Sorbonne Universite, Paris (FR); Centre National De La Recherche Scientifique, Paris (FR); Institut National De La Sante Et De La Recherche Medicale (INSERM), Paris (FR); Assistance Publique—Hopitaux De Paris, Paris (FR); Université De Paris, Paris (FR)

( * ) Notice: Subject to any disclaimer, the term of this patent is extended or adjusted under 35 U.S.C. 154(b) by 0 days.

(21) Appl. No.: 16/329,423

(22) PCT Filed: Sep. 5, 2016

(86) PCT No.: PCT/EP2016/070892
§ 371 (c)(1),
(2) Date: Feb. 28, 2019

(87) PCT Pub. No.: WO2018/041377
PCT Pub. Date: Mar. 8, 2018

(65) Prior Publication Data
US 2020/0010576 A1    Jan. 9, 2020

(51) Int. Cl.
*C08B 37/16* (2006.01)
*A61K 47/69* (2017.01)
*C12N 15/113* (2010.01)

(52) U.S. Cl.
CPC ...... *C08B 37/0012* (2013.01); *A61K 47/6951* (2017.08); *C08B 37/0015* (2013.01); *C12N 15/113* (2013.01); *C12N 2310/14* (2013.01); *C12N 2310/351* (2013.01)

(58) Field of Classification Search
CPC .... A61K 47/6951; C08B 37/12; C12N 15/13; C12N 2310/14; C12N 2310/351
USPC ........................................................... 536/51
See application file for complete search history.

(56) References Cited

PUBLICATIONS

Leourt et al, Chem. Eur. J., 2004, 10, 2960-2971.*
Arima, H. et al., *Potential Use of Polyamidoamine Dendrimer Conjugates With Cyclodextrins as Novel Carrier for siRNA*, Pharmaceuticals 5 (2012) 61-78.
Giacca, M. et al., *Virus-Mediated Gene Delivery for Human Gene Therapy*, Journal of Controlled Release 161 (2012) 377-388.
Kanasty, R. L. et al., *Action and Reaction: The Biological Response to siRNA and Its Delivery Vehicles*, Molecular Therapy, vol. 20, No. 3 (Mar. 2012) 513-524.
Kopp, J. et al., *The SWISS-MODEL Repository: New Features and Functionalities*, Nucleic Acids Research, vol. 34 (2006) D315-D318.
Lecourt, T. et al., *Triisobutylaluminum and Diisobutylaluminum Hydride as Molecular Scalpels: The Regioselective Stripping of Perbenzylated Sugars and Cyclodextrins*, Chem. Eur. J 10 (2004) 2960-2971.
Lee, S-K. et al., *Cell-Specific siRNA Delivery by Peptides and Antibodies*, Methods in Enzymology, vol. 502 (2012) 91-122.
Marineseu, L. G. et al., *Amino-Acetone-Bridged Cyclodextrins—Artificial Alcohol Oxidases*, Eur. J. Org. Chem. (2010) 157-167.
Metwally, A. A., *Efficient Gene Silencing by Self-Assembled Complexes of siRNA and Symmetrical Fatty Acid Amides of Spermine*, Pharmaceutics 3 (2011) 125-140.
Nanthakumar, C. B. et al., *Dissecting Fibrosis: Their Insights From the Small-Molecule Toolbox*, Nature Reviews Drug Discovery (Sep. 2015) 1-28.

(Continued)

Primary Examiner — Ganapathy Krishnan
(74) Attorney, Agent, or Firm — Alston & Bird LLP

(57) ABSTRACT

The invention relates to a capped cyclodextrin-hydrophobic moiety conjugate, to a supramolecular polymer formed of capped cyclodextrin-hydrophobic moiety conjugates according to the invention and to a siRNA-cyclodextrin complex comprising a supramolecular polymer according to the invention. The invention also relates to a method for manufacturing the capped cyclodextrin-hydrophobic moiety conjugate, the supramolecular polymer, the siRNA-cyclodextrin complex according to the invention. The capped cyclodextrin-hydrophobic moiety conjugate of the invention comprises a capped cyclodextrin group and at least one hydrophobic moiety bound by a first linker to one of the carbon atoms of the cap. The invention can be used for various applications in particular in the pharmaceutical field.

21 Claims, 6 Drawing Sheets

Specification includes a Sequence Listing.

(56) References Cited

PUBLICATIONS

Rekharsky, M. V. et al., *Complexation Thermodynamics of Cyclodextrins*, Chem. Rev. 98 (1998) 1875-1917.

Singha, K. et al., *Polymers in Small-Interfering RNA Delivery*, Nucleic Acid Therapeutics, vol. 21, No. 3 (2011) 133-147.

Tam, Y. Y. C. et al., *Advances in Lipid Nanoparticles for siRNA Delivery*, Pharmaceutics 5 (2013) 498-507.

Tran, D. N. et al., *Cyclodextrin-Adamantane Conjugates, Self-Inclusion and Aggregation Versus Supramolecular Polymer Formation*, Org. Chem. Front. 1 (2014) 703-703.

Xiao, S. et al., *Diisobutylaluminum Hydride (DIBAL-H) Promoted Secondary Rim Regioselective Demethylations of Permethylated β-Cyclodextrin: A Mechanistic Proposal*, Eur. J. Org. Chem. (2010) 1510-1516.

International Search Report and Written Opinion for Application No. PCT/EP2016/070892 dated Oct. 24, 2016, 8 pages.

Petter, R. C. et al., *Cooperative Binding by Aggregated Mono-6-(alkylamino)-β-cyclodextrins*, J. Am. Chem. Soc. 112 (1990) 3860-3868.

Kamitori, S. et al., *Structured Study of Monosubstituted p-Cyclodextrins. Crystal Structures of Phenylthio-p-cyclodextrin and Phenysulphinyl-(3-cyclodextrin and Spectroscopic Study of Related Compounds in Aqueous Solution)*, J. Chem. Soc. Perkin Trans. II 1987 (1987) 7-14.

Marinescu, L. G. et al., *Amino-Acetone-Bridged Cyclodextrins-Artificial Alcohol Oxidases*, European Journal Organic Chemistry, vol. 2010, No. 1 (2010) 157-167.

Wenz, G., *Cyclodextrins as Building Blocks for Supramolecular Structures and Functional Units*, Angew. Chem. Int. Ed. Engl. 33 (1994) 803-822.

Tran, D. N. et al., *Cyclodextrin-adamantane conjugates, self-inclusion and aggregation versus supramolecular polymer formation*, Organic Chemistry Frontiers, vol. 1, No. 1 (2014) 703-706.

\* cited by examiner

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: siRNA sense strand

<400> SEQUENCE: 1
cuuacgcuga guacuucgad tdt                                             23

<210> SEQ ID NO 2
<211> LENGTH: 23
<212> TYPE: DNA
<213> ORGANISM: Artificial Sequence
<220> FEATURE:
<223> OTHER INFORMATION: siRNA antisense strand

<400> SEQUENCE: 2
ucgaaguacu cagcguaagd tdt                                             23
```

US 10,947,323 B2

CAPPED CYCLODEXTRIN-HYDROPHOBIC MOIETY CONJUGATE, CYCLODEXTRIN SUPRAMOLECULAR POLYMER, AND CYCLODEXTRIN-SIRNA COMPLEX AND METHOD OF SYNTHESIS THEREOF

FIELD

The invention relates to a capped cyclodextrin-hydrophobic moiety conjugate, to a supramolecular polymer formed of capped cyclodextrin-hydrophobic moiety conjugates according to the invention and to a siRNA-cyclodextrin complex comprising a supramolecular polymer according to the invention.

The invention also relates to a method for manufacturing the capped cyclodextrin-hydrophobic moiety conjugate, the supramolecular polymer, the siRNA-cyclodextrin complex according to the invention.

BACKGROUND

Antiviral treatment using small interfering RNAs, noted siRNAs in the following of this text, are very promising for efficiently fighting diseases such as viral infections.

The well known obstacle to their use is the low efficiency of the used transfection agent, these agents being viral or not.

With viral vectors, some problems of immune response have been encountered[1],[2]. With synthetic non viral vectors, a low immune response is observed, as well as a low efficiency, and some cytotoxicity for high or repeated dosages.

[1] *J. controlled reseased.* 2012 161, 377-388
[2] *Mol. Ther.* 2012, 20, 513-524

Such vectors are often cationic polymers in order to neutralize the negative charges of the RNAs and for enabling it to penetrate cells, generally by endocytosis.

Examples of such vectors are, in particular, polyethylenimine (PEI)[3], dendrimers[4], chitosane derivatives, polylysine, branched polyaminoamides. Some of them are commercialized for in vitro studies where they show low toxicities. But their use in vivo is often accompanied of a real toxicity due to the polymeric character of the cations.

[3] *Nucleic Acid Therapeut.* 2011, 21, 133-147
[4] *Pharmaceuticals.* 2012, 5, 61-78

Other transfections vectors are known, using liposomes[5] or systems conjugated to antibodies[6], peptides[7], or aptamers[8]. Some synthetic transfections agents are under clinical studies. In particular, a cationic polymer containing cyclodextrin has been recently studied[9]. This latter technique is based on the use of cyclodextrins for covering the polymer with stabilizators (polyethylene glycol (PEG) chains) and targeting agents (transferrin).

[5] *Pharmaceutics.* 2013, 5, 498-507
[6] *Methods in Enzymology.* 2012, 34, 10.
[7] *Nucleic and researches,* 2006, 34, 10.
[8] *Nat. Rev. Drug Discover.* 2015, 14, 1, 703.
[9] *Org. Chem. Front,* 2014, 1, 703

However, this polymer remains a cationic polymer which can be toxic in fine.

SUMMARY

The invention aims to palliate the drawbacks of the prior art transfection agents by proposing transfection agents which are both polycationic and non polymeric.

For this aim, the invention proposes a supramolecular polymer made of functionalized cyclodextrins, as transfection agent.

Cyclodextrins are very available natural molecule.

Cyclodexrin is a tronconic molecule having two hydrophilic rims: a primary rim (smallest rim), and a secondary rim (largest rim). It is made of glucopyranose units which are designated, according to the most used nomenclature, by capital letters in the trigonometric sense, the cyclodexrin being visualized from the primary rim.

There are biocompatible because formed of glucose units.

Cyclodextrin may be made of 6, 7 or 8 glucopyranose units. They are respectively noted α-, β-, or γ-cyclodextrin.

More importantly, they possess a hydrophobic cavity while being hydrosoluble.

It is why they form inclusion complexes, with hydrophobic molecules, in water.

This property is used in the pharmaceutical industry, in particular for solubilizing hydrophobic active principle.

Although theoretically when a hydrophobic moiety is bound to a cyclodextrin, the cyclodextrin forms a supramolecular polymer, the inventors have shown in "Cyclodextrin-adamantane conjugates, self-inclusion and aggregation versus supramolecular polymer formation", *Org. Chem. Front,* 2014, 1, 703-706, that the hydrophobic moiety tends to self-includes in the hydrophobic cavity of the cyclodextrin, thereby impairing the formation of a supramolecular polymer.

Accordingly, the first problem to be solved by the invention for obtaining a supramolecular polymer made of functionalized cyclodextrins is to solve the problem of the self-inclusion of the hydrophobic moiety in the hydrophobic cavity of a cyclodextrin to which it is bound.

Therefore the aim of the invention is the use of a capped cyclodextrin derivative which is functionalized with a hydrophobic moiety and which is also a cationic derivative, as a molecular brick for obtaining a cyclodextrin supramolecular polymer which can be used as transfection agent for siRNA.

The crux of the invention is the use of a cap on the cyclodextrine derivative in order to avoid the self-inclusion of the hydrophobic moiety.

A capped cyclodextrin has already been described in "Amino-acetone-bridged cyclodextrins-artificial alcohol oxidase", *Eur., J., Org, Chem.,* 2010, 157-167.

However, in this article, the capped cyclodextrin was not used for forming supramolecular polymer, i.e. was not functionalized with a hydrophobic moiety, this latter hydrophobic moiety being intended to enter the internal cavity of another capped functionalized cyclodextrin.

On the contrary, the capped cyclodextrin disclosed in this article was used as a catalyst acting as a host for molecules not bound to another cyclodextrin molecule.

In the present text, the terms "capped cyclodextrin group" designate a cyclodextrin group with a cap binding two carbon atoms previously bearing a hydroxyl group of its primary rim.

Such a cyclodextrin derivative is called "bridged cyclodextrin" in the article "Amino-acetone-bridged cyclodextrins-artificial alcohol oxidase" previously cited.

In contrast, in the invention, the term "bridged" when used in relation with a cyclodextrin derivative means that the cyclodextrin unit is linked to another cyclodextrin unit.

In this context, the invention proposes, a cationic molecular brick for obtaining a cyclodextrin supramolecular polymer usable as vector for inter alia transfection of siRNA.

This cationic molecular brick is a capped cyclodextrin-hydrophobic moiety conjugate comprising a cyclodextrin group bearing at least one hydrophobic moiety such as an adamantane group, a $C_2$-$C_{13}$ alkyl group optionally containing at least one heteroatom, a $C_5$-$C_6$ aromatic group optionally containing at least one heteroatom[10] or a $C_3$-$C_8$ non-aromatic cycle optionally containing at least one heteroatom, wherein:

the cyclodextrin derivative is capped on its primary rim by a cap binding a first carbon atom previously bearing a hydroxyl group, of a first glucopyranose unit to a second carbon atom, previously bearing a hydroxyl group, of a second and different glucopyranose unit, said first and second glucopyranose units being preferably separated from each other by at least two glucopyranose units, and the hydrophobic moiety is bound by a first linker to one of the atoms of the cap.

[10] Chem. Rev., 1998, 98 (5), pp 1875-1918

Said first and second carbon atoms are preferably the carbon atoms in position 6 of the glucopyranose units.

The hydrophobic moiety can be a $C_2$-$C_{13}$ alkyl optionally containing at least one heteroatom, a $C_5$-$C_6$ aromatic or a $C_3$-$C_8$ non aromatic cycle optionally containing at least one heteroatom such as those listed in Chem. Rev., 1998, 98 (5) pp 1875-1918.

The hydrophobic moieties which are preferred in the invention are adamantane or phenyl moieties.

The more preferred hydrophobic moiety is an adamantane moiety.

Indeed, adamantane as a well-known affinity for the hydrophobic cavity of a cyclodextrine.

The capping of the primary rim of the cyclodextrin derivative prevents the hydrophobic group to self-include into the hydrophobic cavity of the cyclodextrin group, by the primary rim, and the secondary rim. The self-inclusion by the secondary rim of a hydrophobic moiety beared by a cyclodextrin occurs when a glucopyranose unit bearing the hydrophobic moiety makes a 360° rotation[11]. And, as demonstrated in the following, the cap prevents this rotation and therefore the self-inclusion by the secondary rim.

[11] Org. Chem. Front, 2014, 1, 703-706

Said cap preferably forms, together with the carbon atoms to which it is bound, a chain having from 2 to 20 links, more preferably from 2 to 12 links, even more preferably 7 links.

The term "link" is used in the invention because the atoms of the links may be heteroatoms.

Furthermore, the chain forming the cap can also comprises at least one functional group, this functional group also forming a link of the chain. Such a functional group is preferably chosen in the group consisting of a ketone group, an amine group, an ether group, an amide group, an ester group, a nitrile group, an acid anhydride group, an amidine group, a peroxide group, a sulfone group, a sulfoxide group, a disulfide group, a carboxyl group, an urethanes group, an oxime group, an alkyl group, an alkenyl group, an alkynyl, aryl, an aralkyl group, a heterocyclyl and heterocyclylalkyl sulfide groups, a sulfonyl group, a sulfonamide group, a hydrazine group, a hydrazide group, an ureas group, a guanidine group, an enamine group, an isocyanate group, an isothiocyanate group, a cyanate group, a thiocyanate group, a phosphine group, a phosphite group, a phosphinite group, a phosphonate group, a phosphinate group, a phosphate group.

The chain of the cap may also comprise one or more series of atoms connected to form a cycle. Said cycle can be a non aromatic or an aromatic cycle and may comprise at least one heteroatom. It is also a link in the meaning of the invention.

Examples of aromatic or non aromatic (hetero) cycle are a triazol ring, a phenyl group, a biphenyl group, a cyclopentadienyl group, a furan derivative, a thiophen derivative, a pyrrole derivative, a selenophene derivative.

Thus, a "link" may be a C—H or C—$H_2$ group, or a heteroatom, or a functional group, or a non aromatic or aromatic (hetero) cycle.

Preferably, the cyclodextrin group is an α- or β-cyclodextrin group.

In order to have the most efficient capping of the primary rim, the cap preferably binds the carbon atoms previously bearing a hydroxyl group in position 6 of the glucopyranose units which are in position A and D of the primary rim of the cyclodextrin group.

Preferably, in order to functionalize the capped cyclodextrin group with the hydrophobic moiety, the cap preferably comprises a first heteroatom and the hydrophobic moiety is bound to this first heteroatom through a first linker.

The first linker forms, with the heteroatom to which it is bound a chain having from 2 to 20 links, preferably from 2 to 12 links, more preferably 3 links.

The first linker can also comprise at least one heteroatom and/or at least one functional group and/or at least one aromatic or non aromatic (hetero) cycle.

The definition of the terms "links", "heteroatom", "functional group" and "aromatic or non aromatic (hetero) cycle" are the same for the first linker as for the cap.

With this first embodiment of the capped cyclodextrin-hydrophobic moiety conjugate of the invention, a cyclodextrin-supramolecular polymer can be obtained as will be discussed in the following of this text.

However, for forming a siRNA-cyclodextrin complex from such a supramolecular polymer, the invention proposes, in a second embodiment, a capped cyclodextrin-hydrophobic moiety conjugate which is functionalized with a positively charged group R.

The positively charged group R is preferably bound to a second heteroatom of the cap of the capped cyclodextrin-hydrophobic moiety conjugate, through a second linker.

Examples of such a positively charged group R are an amine group, an arginine group, a guanidine group, a linear or branched chain comprising between 1 and 20 atoms for the main chain, these atoms being nitrogen atoms and/or oxygen atoms and/or carbon atoms. Such a chain may comprise from 1 to 30 amine groups or guanidine groups.

Preferably, R is chosen among an, an amine group, an arginine group, a guanidine group, or one of the following groups:

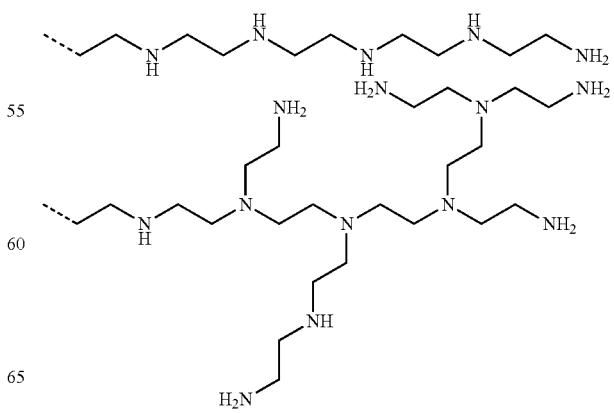

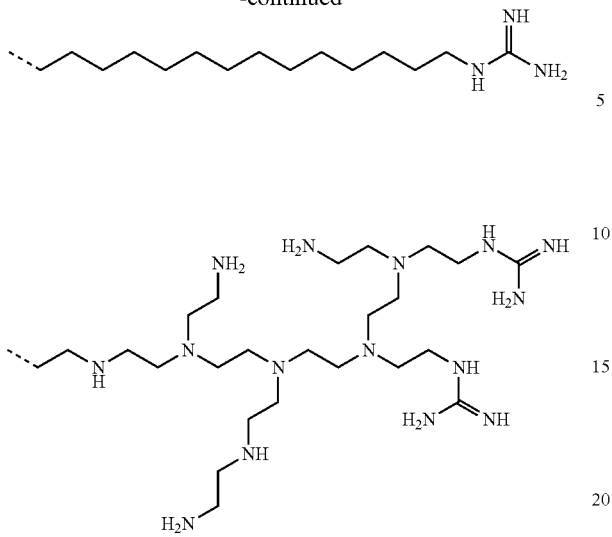

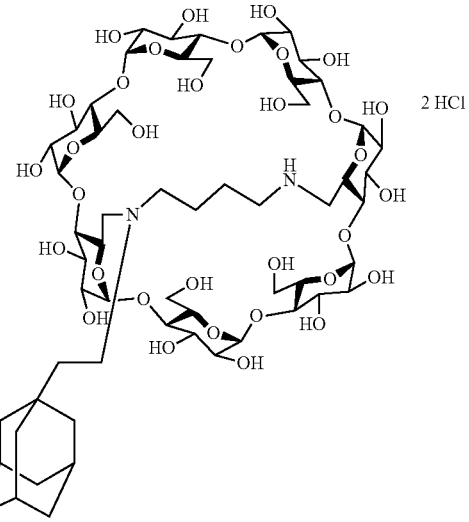

Formula I-1

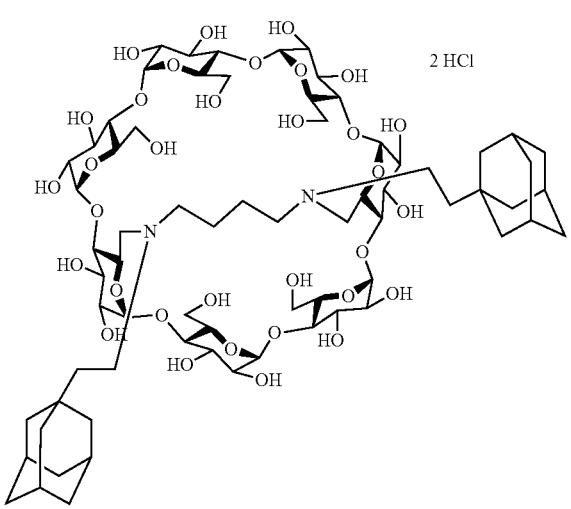

Formula I-2

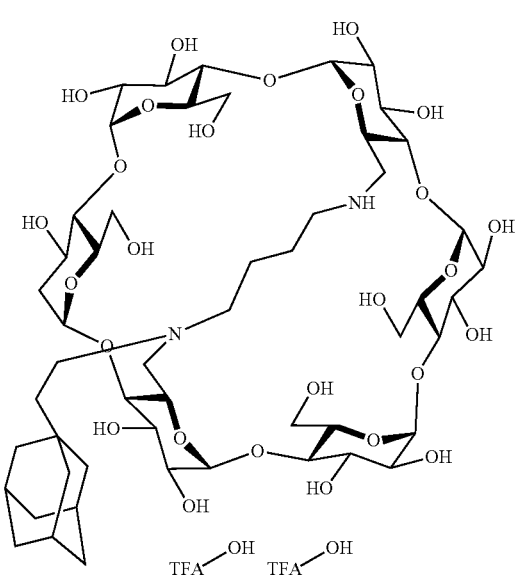

Formula I-3

When the positively charged group R comprises amine group(s), or guanidine group(s) then the number of counter ion(s) x is the number of amine group(s) plus the number of guanidine group(s).

The cap, in this second embodiment preferably comprises a second heteroatom which may be different or identical to the first heteroatom of the cap to which the first linker is bound.

The second linker can be identical or different from the first linker.

In a general manner, the second linker forms, with the heteroatom to which it is bound a chain having from 0 to 20 links, preferably from 2 to 12 links.

When the second linker has 0 link, it is for example because the positively charged group is formed by the second heteroatom of the cap.

For example, when the second heteroatom of the cap is a nitrogen atom, the positively charged group is a primary or a secondary amine group forming a link of the cap.

In the cap as in the first and second linkers, preferably the heteroatom is a nitrogen atom.

In the second embodiment of the capped cyclodextrin-hydrophobic moiety of the invention, due to the presence of the positively charged group(s), namely ammonium salt(s), the capped cyclodextrin-hydrophobic moiety conjugate of the invention also comprises counter ion(s).

Preferred counter ions are triflate or hydrochloride ions.

The preferred capped cyclodextrin-hydrophobic moiety conjugates of the invention have one of the following formulae I-1 to I-26, The maximum number of Cl$^-$ (or TFA-O$^-$) group per molecules is mentioned in the following formulae I-1 to I-25, but for simplification purposes, the molecules are shown as a salt of the cyclodextrin hydrophobic moiety conjugate with either hydrochloride acid or triflate hydroxide.

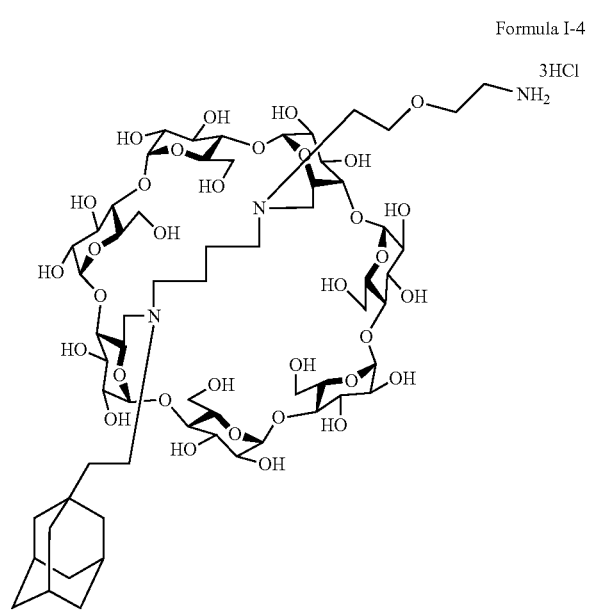
Formula I-4
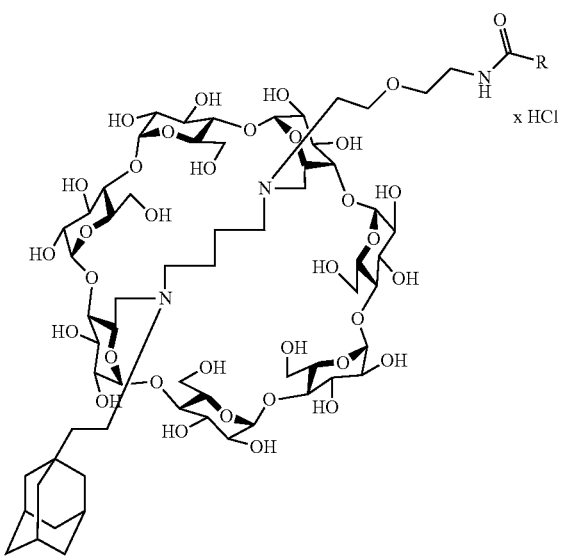
Formula I-6 in which R and x are as previously defined
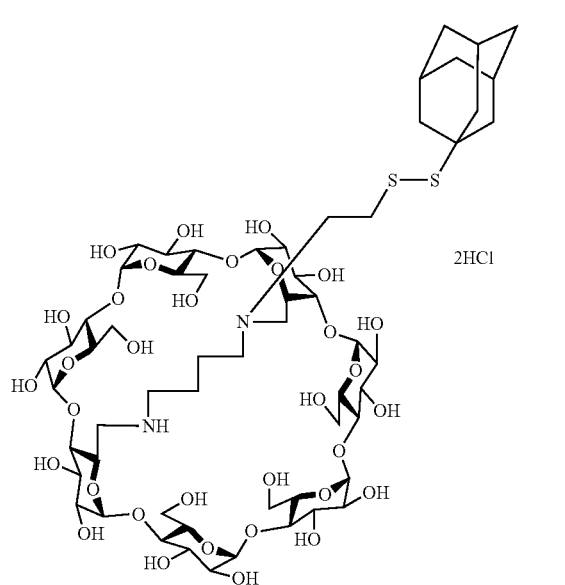
Formula I-5
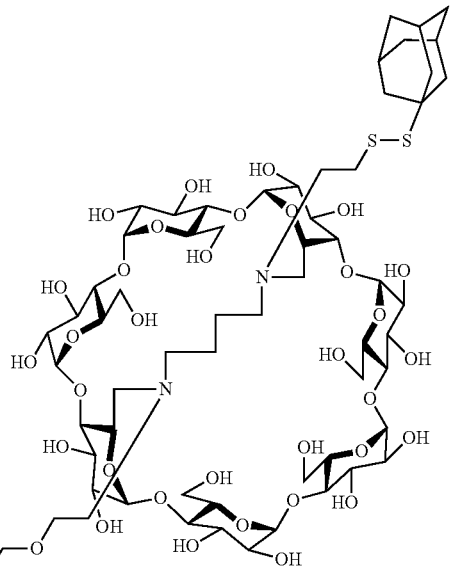
Formula I-7 in which R and x are as previously defined Formula I-8
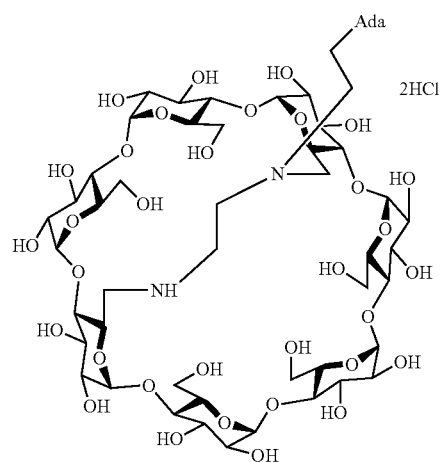
Formula I-9
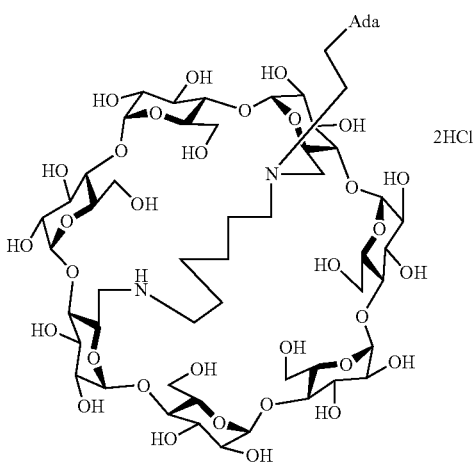
Formula I-10
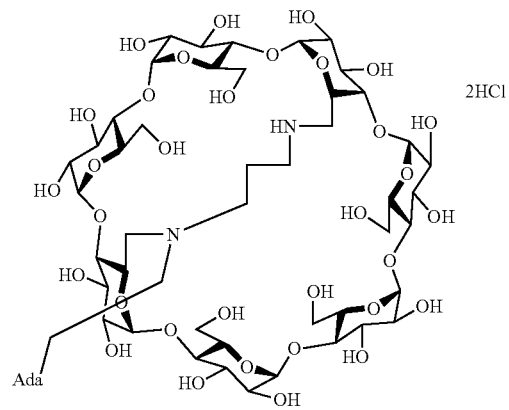
Formula I-11
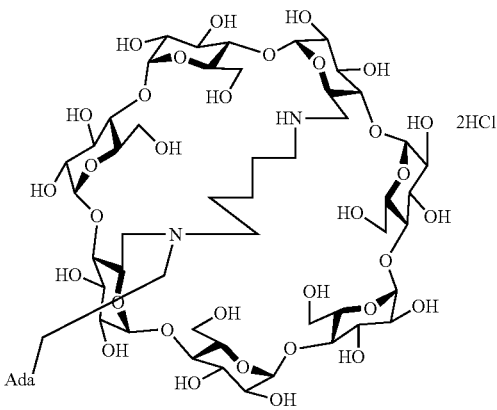
Formula I-12
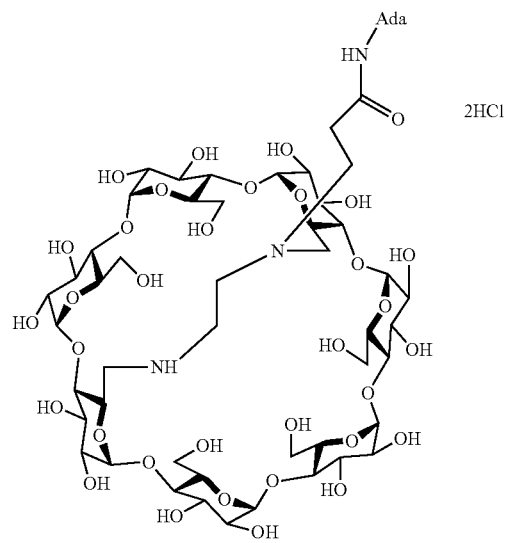
Formula I-13
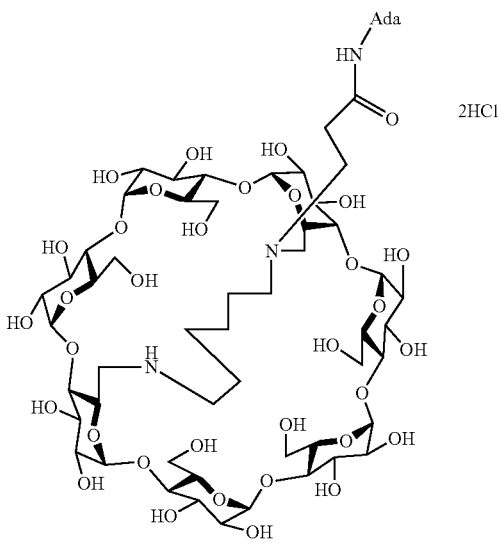

-continued
Formula I-14
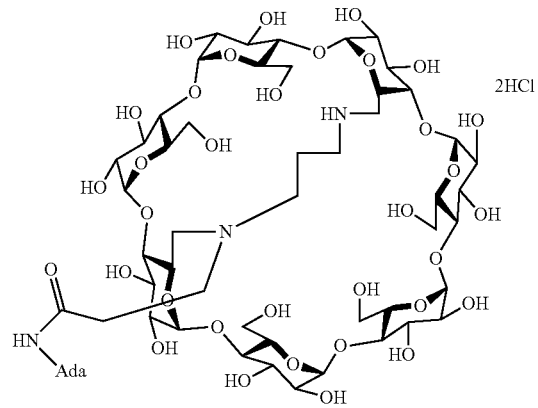
Formula I-15
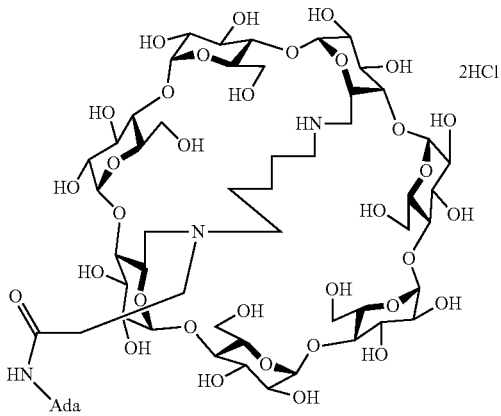
Formula I-16
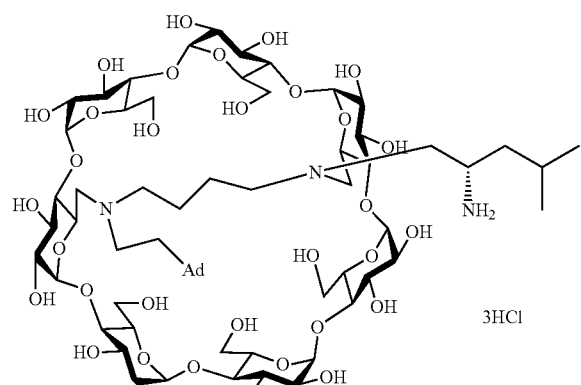
Formula I-17
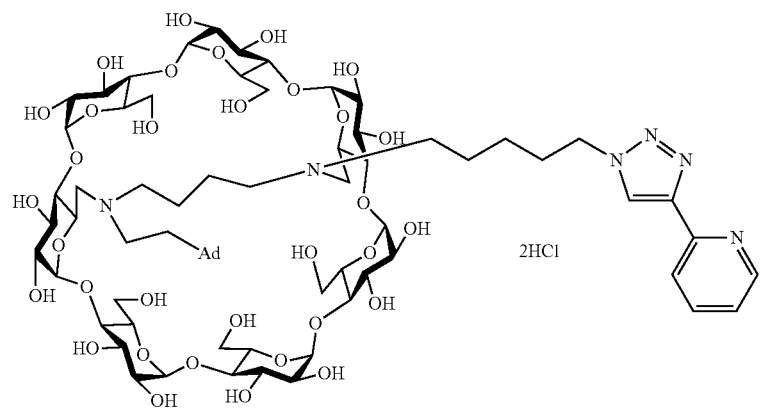
Formula I-18
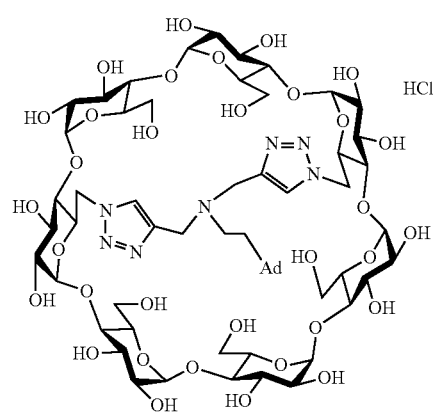
Formula I-19
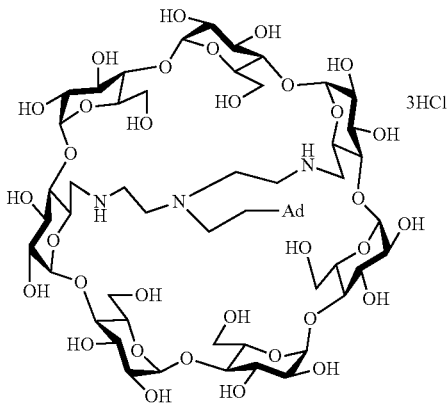

Formula I-20
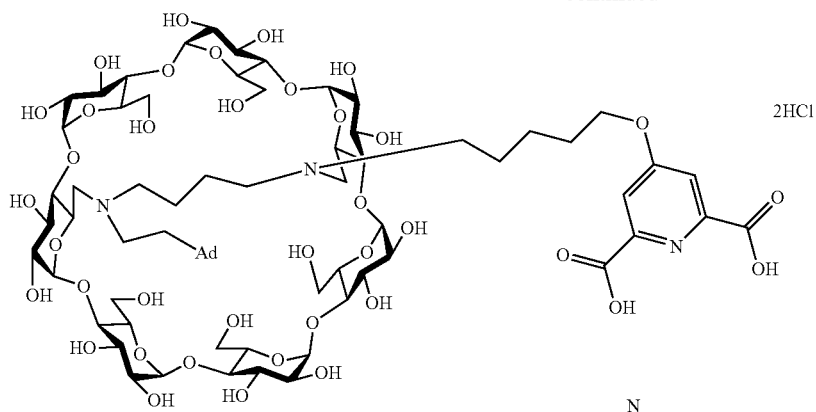
2HCl
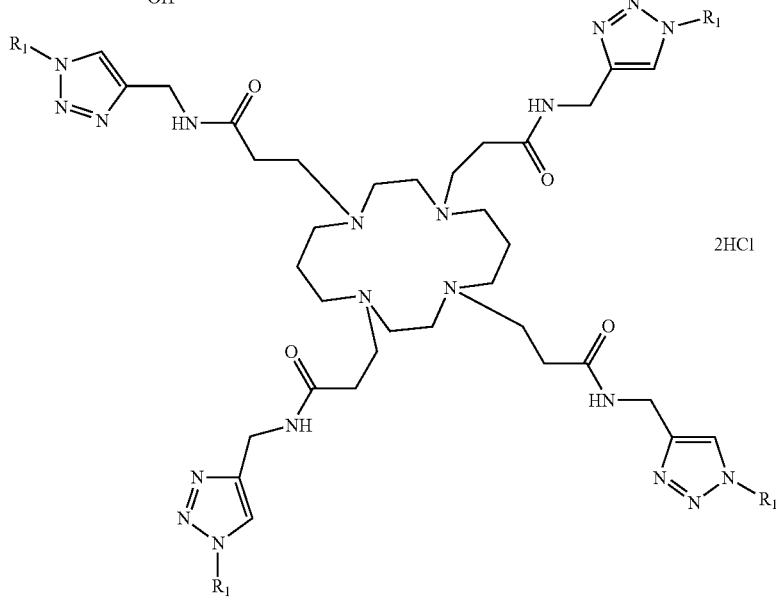
2HCl
Formula I-21 in which $R_1$ has the following formula
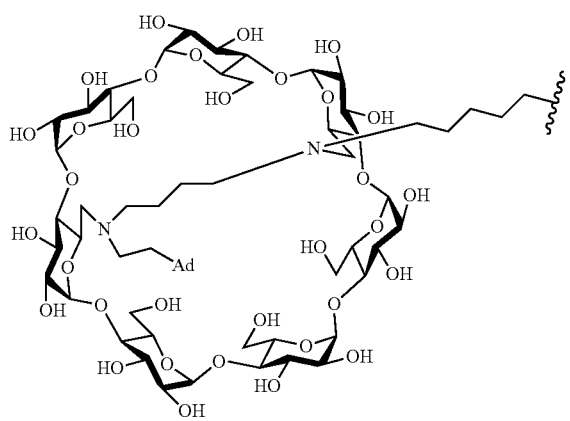
Formula I-22
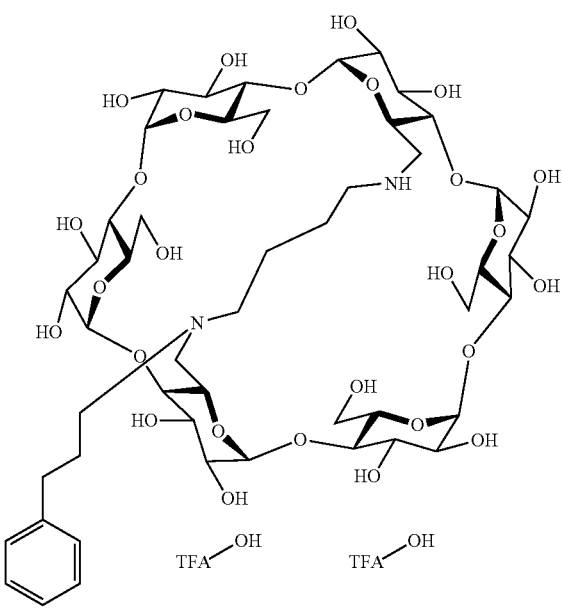

Formula I-23
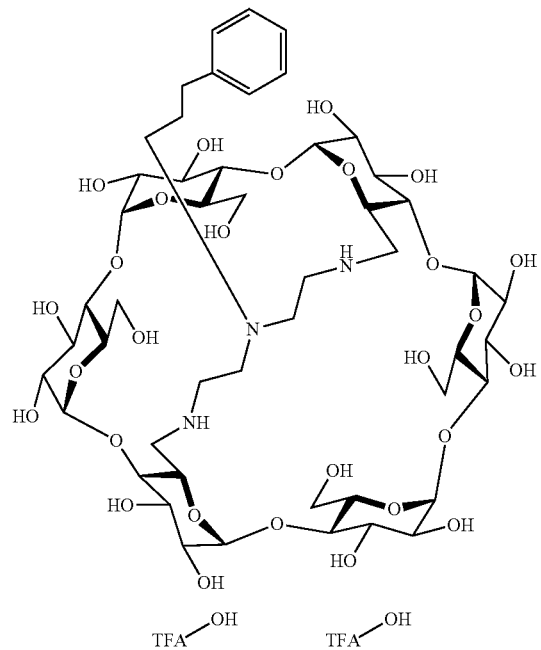
Formula I-24
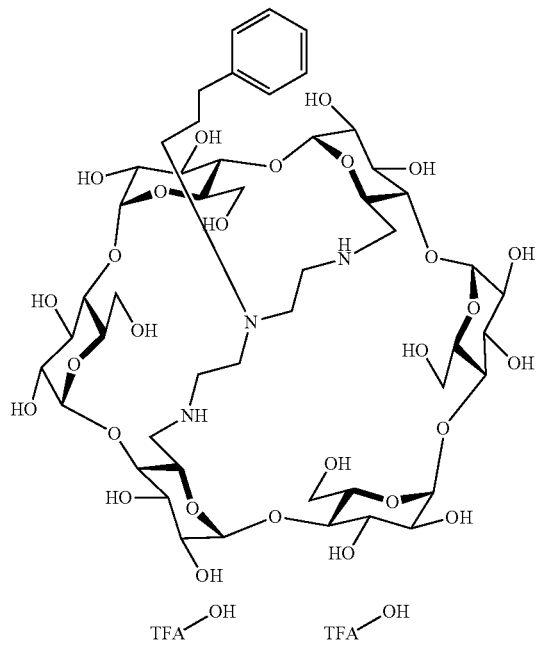
Formula I-25
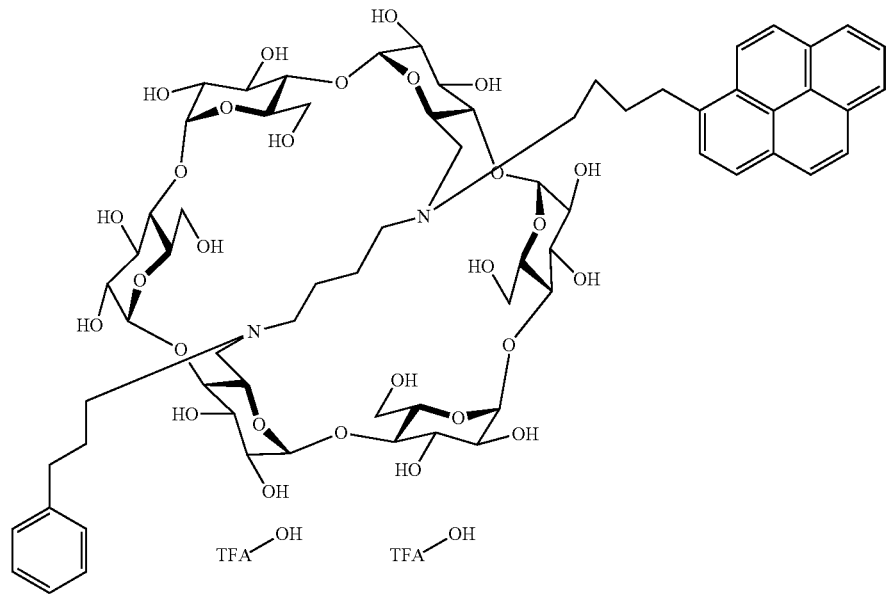

Formula I-26

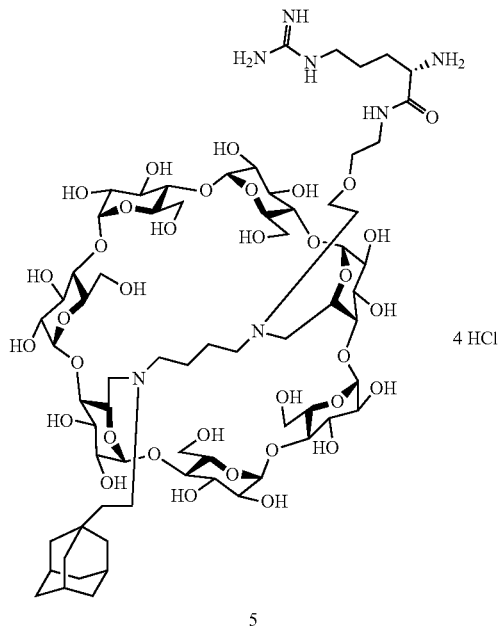

In formulas I-4 to I-11, "Ada" designates an adamantane group and in formulas I-12 to I-17, "Ad" designates an adamantane group.

A particularly preferred capped cyclodextrin-adamantane conjugate has the following formula I-1:

Formula I-1

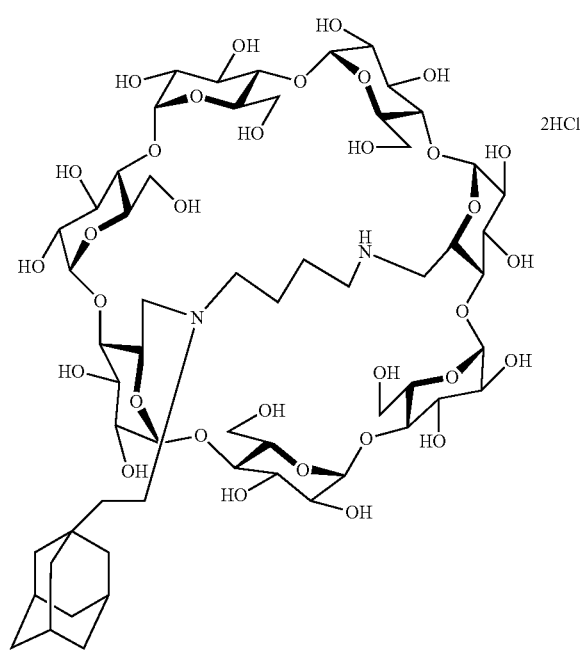

These conjugates of formulas I-1 to I-26 are cationic due to the presence of $NH_2^+$ groups.

They are obtained under the form of a salt. A preferred salt is a hydrochloride salt. Such hydrochloride salts are solid at ambient temperature (from 15 to 30° C.) and stable under ambient atmosphere, i.e. they do not degrade when stored and transported under ambient temperature and atmosphere.

This a particularly advantageous property: no particular care has to be taken when storing, transporting or manipulating them.

And, when solubilized in water or in an aqueous solution, they form a supramolecular polymer made of units of conjugates according to the invention, the hydrophobic moiety of each conjugate of the invention entering the hydrophobic cavity of the capped cyclodextrin group of another conjugate of the invention.

In this manner a supramolecular polymer is obtained.

When the supramolecular polymer of the invention is obtained from capped cyclodextrin-hydrophobic moiety conjugates functionalized with a positively charged group, for example when it comprises a cap or a first or a second linker comprising nitrogen atoms, it is uniformly positively charged.

Accordingly, it forms a complex with a siRNA.

Indeed, RNA is composed of deoxyribose groups bearing negatively charged phosphate groups which associate with the positively charged groups of the supramolecular polymer of the invention.

Accordingly, a second object of the invention is a supramolecular polymer consisting of the capped cyclodextrin-adamantane conjugates of the invention and a third object of the invention is a siRNA capped cyclodextrin complex comprising a supramolecular polymer according to the invention.

A preferred supramolecular polymer of the invention is made of capped cyclodextrin-adamantane conjugates of following formula I-1:

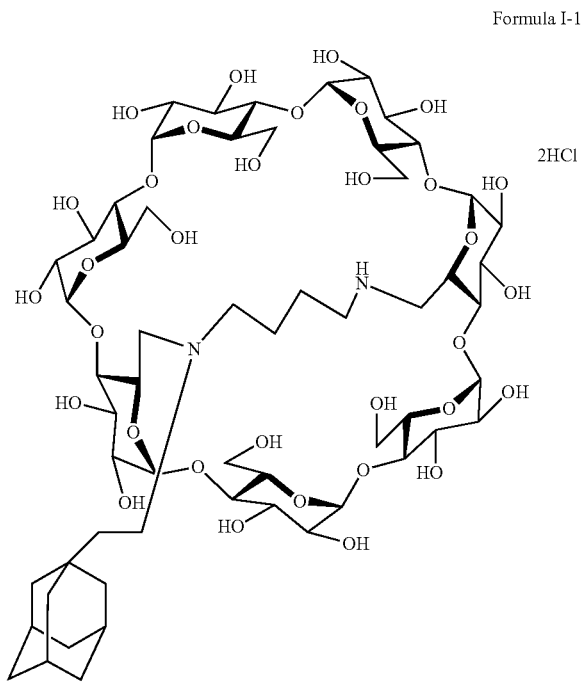

Formula I-1

The invention also proposes a method for manufacturing a capped cyclodextrin-adamantane conjugate of formula I-1, under the form of a salt.

This method comprises the following steps:

a) benzylation of the hydroxyl groups of an α- or β-cyclodextrin, thereby obtaining a perbenzylated α- or βcyclodextrin, b) debenzylation of the benzyl groups in position A and D of the primary rim of the perbenzylated α- or βcyclodextrin obtained in step a), by regioselective reduction, thereby obtaining a perbenzylated diol α- or β-cyclodextrin.

This regioselective reduction proceeds by steric induction as disclosed in Chem. Eur. J. 2004, 10, 2960-2971.

Then the following steps are carried out:

c) oxydation of the hydroxyl groups in aldehyde in position A and D of the primary rim of the perbenzylated diol α- or β-cyclodextrin obtained in step b), by Swern oxidation, thereby obtaining a perbenzylated dialdehyde α- or β-cyclodextrin, d) double reductive amination with putrescine of the compound obtained in step c), thereby obtaining a capped perbenzylated α- or β-cyclodextrin, wherein the cap has the formula $NH(CH_2)_4NH$, in which each N atom is bound to one of the carbon atoms previously functionalized with an aldehyde group of the compound obtained in step c), e) reductive amination in presence of an O=adamante group of the capped perbenzylated α- or β-cyclodextrin obtained in step d), thereby obtaining a mixture of:

a capped perbenzylated α- or β-cyclodextrin functionalized with one adamantane group, and a capped perbenzylated α- or β-cyclodextrin functionalized with two adamantane groups, each adamantane groups being bound to each heteroatom of the cap, f) purification of the mixture of compounds obtained in step e) by chromatography on a silica gel column, thereby obtaining the desired perbenzylated capped α- or β-cyclodextrin-adamantane conjugate functionalized with one adamantane group, g) debenzylation of the perbenzylated capped cyclodextrin-adamantane conjugate obtained in step f) by catalytic hydrogenation in water/THF in presence of trifluoroacetic acid, thereby obtaining a trifluoroacetate salt of the desired cyclodextrin-adamantane conjugates.

When a hydrochloride salt is desired, then the process of the invention furthermore comprises a step h) of exchange of the trifluoroacetate ions with chlorhydrate ions by elution of the debenzylated (deprotected) compound obtained in step g) on an ion exchange column.

Step h) may also be carried out by contacting the compound obtained in step g) with an aqueous solution of hydrochloric acid followed by a lyophilization.

The invention also proposes a method for manufacturing a supramolecular polymer wherein the monomers are capped cyclodextrin-hydrophobic moiety conjugates according to the invention.

This method comprises a step of solubilization of the capped cyclodextrin-hydrophobic moiety conjugates in an aqueous solution.

Such an aqueous solution can be water or a culture medium. Preferably, the concentration of capped cyclodextrin-hydrophobic moiety conjugates according to the invention in the aqueous solution is of from 0.070 mM to 6 mM. Preferably this concentration is of 5 mM.

Furthermore, the invention proposes a method for manufacturing a siRNA-cyclodextrin complex which comprises a supramolecular polymer according to the invention.

This method comprises the following steps:

a) solubilization of capped cyclodextrin-hydrophobic moiety conjugates according to anyone of claims 1-10 in a DMEM medium (Dubelccos's modified Eagle's medium), FBS (Fetal bovine serum) 10% without antibiotics, b) incubation of the solution obtained in step a) during 5 minutes at a temperature comprised between 15° C. and 35° C., c) solubilizing siRNAs in an Opti-MEM medium poor in FBS, Two amounts of siRNA have been prepared: 5 pmol and 10 pmol.

d) incubation of the solution obtained in step c) during 5 minutes at a temperature comprised between 15° C. and 35° C., and e) mixing the incubated solutions obtained in steps b) and d) for 20 min at a temperature comprised between 15° C. and 35° C. Different ratio nitrogen/phosphate (N/P) of cyclodextrin-siRNA have been chosen varying from 6 to 1190.

BRIEF DESCRIPTION OF THE DRAWINGS

In order to prove several essential points of the invention such as the inclusion of the hydrophobic moiety (such as an Adamantane group) and the formation of the supramolecular polymer from the capped cyclodextrin-adamantane conjugates according to the invention, some experiments were carried out and their results are given below as examples of how to carry out the invention.

These examples will be described with reference to the annexed figures in which.

DETAILED DESCRIPTION

Figure 1:
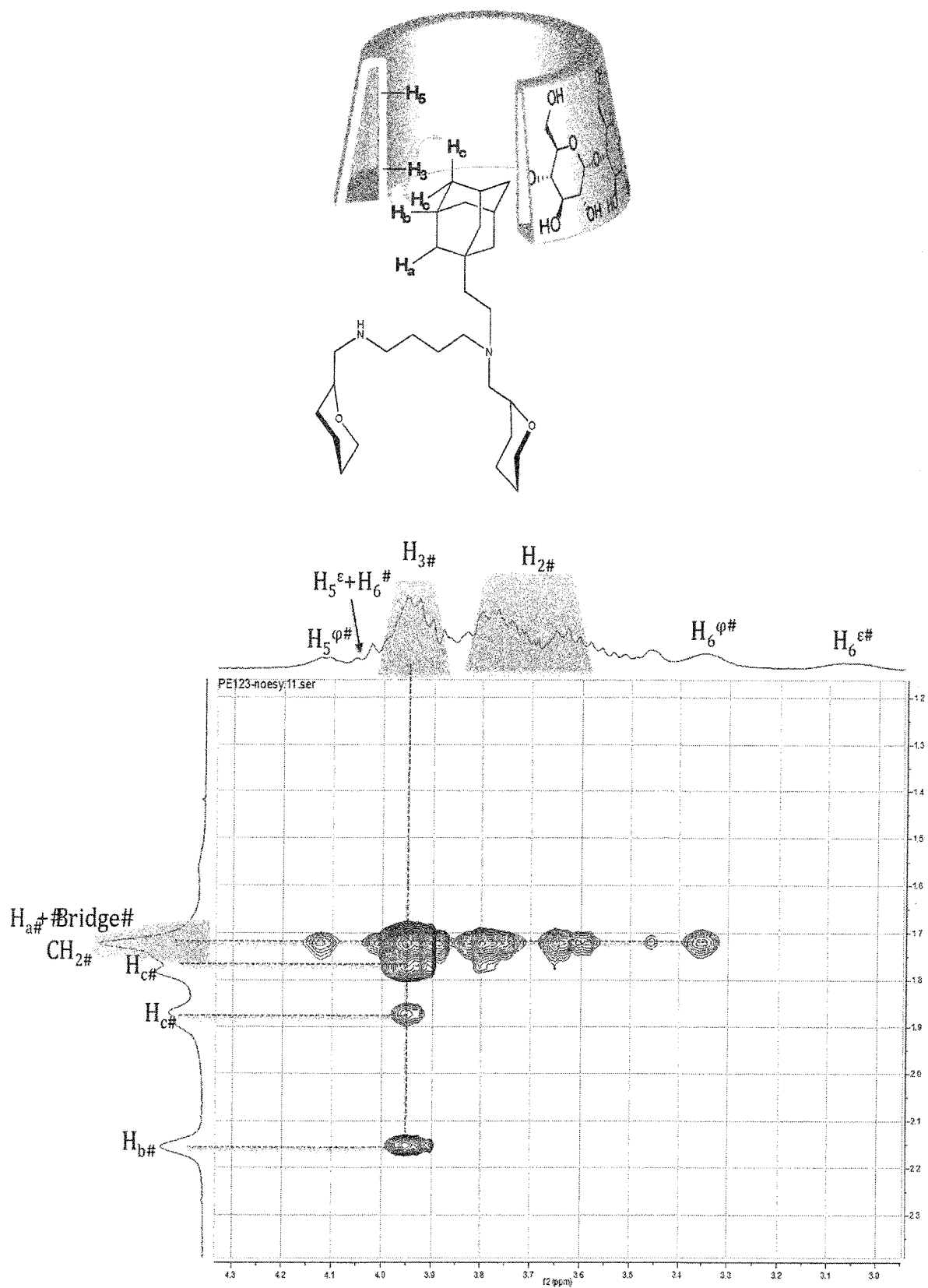
FIG. 1 shows the ROESY NMR spectrum of the supramolecular polymer obtained in example 3.

These examples are only illustrative, and not limitative, of the invention.

The reactants were purchased from commercial sources and used without further purification.

Tetrahydrofurane (THF) was freshly distilled by standard methods on sodium/benzophenone.

To characterize the compounds obtained during the synthesis of the compounds of the invention, NMR was used.

NMR spectra were recorded on a Bruker Am-400 MHz or a Bruker Avance 600 MHz using CDCl$_3$, DMSO-d6, and D$_2$O as solvents.

Assignments of the signals were done using Correlation Spectroscopy (COSY), Nuclear Overhauser Spectroscopy (NOESY), Heteronuclear Single Quantum Coherence Spectroscopy (HSQC), Heteronuclear Multiple Bound Correlation (HMBC), Total Correlation Spectroscopy (TOCSY), Transverse Rotating-frame Overhauser Enhancement Spectroscopy (T-ROESY).

Diffusion ordered Spectroscopy (DOSY) NMR diffusion measurements were carried out by using the Longitudinal EDdy BiPolar gradient pulse (LEDBPGP) sequence.

Sixteen spectra were acquired with gradient pulse (delta) of 4 ms ranging in strength from 0.28 to 5.26 g/mm for BBFO 5 mm NMR probe.

A diffusion delay (delta) from 50 to 150 ms was used and the diffusion coefficients (D) were calculated with topspin 3.0.

Example 1

Synthesis of a Conjugate According to the Invention in which the Cyclodextrin Group is a β-Cyclodextrin Group.

In the following of the present text "CD" designates a cyclodextrin group.

Step a): Synthesis of Perbenzylated Cyclodextrin: Compound (2): β CD Per Bn.

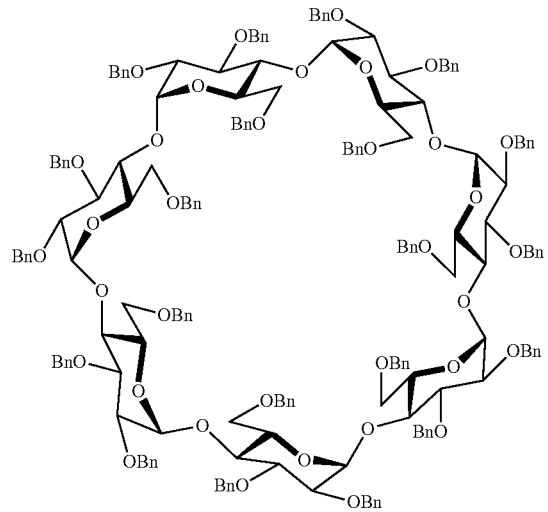

Protocol

β CD (compound 1) was lyophilized before use. Sodium hydride (21.4 g, 535 mmol, w/w 60% in oil) was added portionwise to a stirred solution of β CD (10.4 g, 9.16 mmol) in DMSO (200 ml) at room temperature (rt), under N$_2$. (chloromethyl)benzene (52 ml, 448 mmol) was then added carefully with vigorous mechanic stirring. Reaction was stirred overnight.

The mixture was carefully hydrolysed with MeOH (40 ml) and diluted in water (200 ml). The solution was extracted with Et$_2$O (3×200 ml). The combined organic layers were washed with brine (2×200 ml), dried under MgSO$_4$ and concentrated. The resulting crude product was purified with a silica gel chromatographic column and eluted with Cyclohexane/AcOEt (95:5 then 3:1) to afford to compound (2) β CD per Bn (26.6 g, 96%).

The structure of the product was confirmed by comparison with the literature[12].

[12] *Chem. Eur. J.* 2004. 10, 2960-2971.

Step b): Synthesis of the Perbenzylated Diol β-Cyclodextrin: Compound (3): β CD Diol Per Bn.

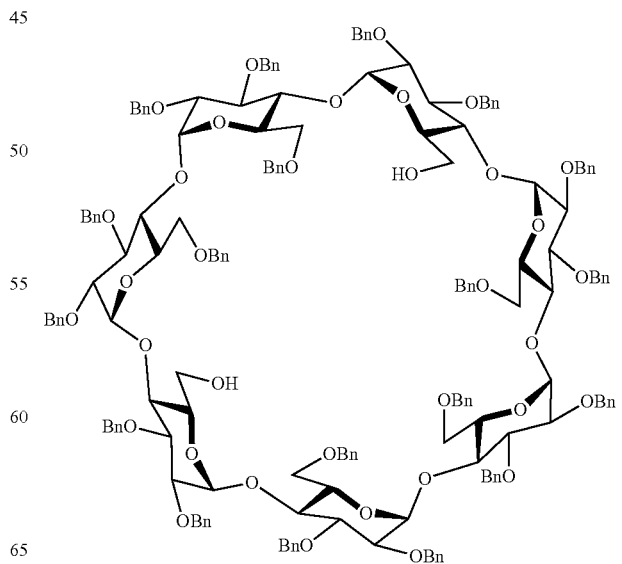

Protocol:

Compound (2) β CD per Bn (15.2 g, 5.02 mmol) was solubilized in Toluene (35 ml). Diisobutylaluminum hydride (66 ml, 93 mmol) was added at rt. The mixture was heated at 60° C. under $N_2$ flux during 1h30. The mixture was then poured carefully into an ice/water erlenmeyer (500 ml). EtOAc (500 ml) and HCl (300 ml) were then added. Solution was stirred overnight. The solution was extracted with 3×300 ml d'AcOEt, washed with brine, dried with Mg504 and concentrated. The resulting crude product was purified with a silica gel column (400 ml) and eluted with Cyclohane/AcOEt (9:1 then 3:1) to afford to the compound (3) CD diol per Bn (10.4 g, 74%).

The structure of the product was confirmed by comparison with the literature[13].

[13] *Eur. J. Org. Chem.* 2010, 1510-1516.

Step c): Synthesis of a Perbenzylated Dialdehyde β-Cyclodextrin: Compound (4): β Dialdehyde Per Bn.

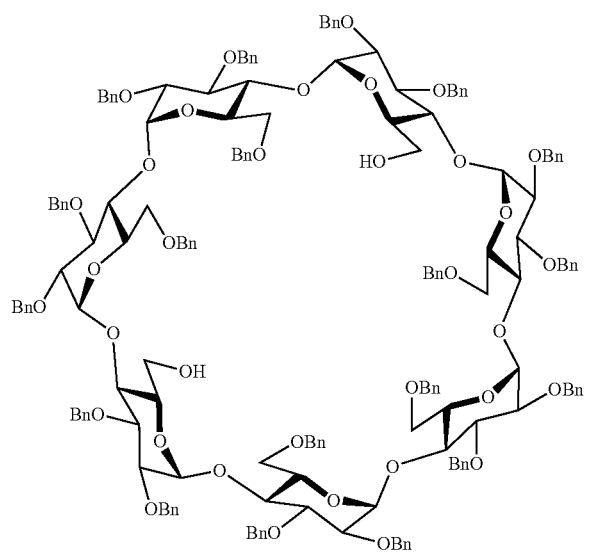 [SMILES: OC[C@H]1O[C@@H]2O[C@H]3C(OCc4ccccc4)C(OCc4ccccc4)[C@H](O[C@@H]3COCc3ccccc3)O[C@H]3C(OCc4ccccc4)C(OCc4ccccc4)[C@H](O[C@@H]3COCc3ccccc3)O[C@H]3C(OCc4ccccc4)C(OCc4ccccc4)[C@H](O[C@@H]3COCc3ccccc3)O[C@H]3C(OCc4ccccc4)C(OCc4ccccc4)[C@H](O[C@@H]3CO)O[C@H]3C(OCc4ccccc4)C(OCc4ccccc4)[C@@H](O[C@@H]4C(COCc5ccccc5)O[C@H](O[C@H]1C(OCc1ccccc1)C2OCc1ccccc1)C(OCc1ccccc1)C4OCc1ccccc1)O[C@@H]3COCc1ccccc1]

Protocol:

Oxalyl dichloride (3 ml, 35.5 mmol) was dissolved in DCM (30 ml) under Argon at −78° C. (methylsulfinyl) methane (5 ml, 70.4 mmol) was diluted in DCM (30 ml) and added over 30 min to the solution. Solution was stirred for 30 minutes. β CD diol per Bn (compound 3) (10.5 g, 3.69 mmol) was dissolved in DCM (40 ml) and added slowly to the solution. Reaction was stirred for 1h30. Triethylamine (5.9 ml, 42.8 mmol) was added and the solution was stirred overnight and warmed slowly to rt. Solution was quenched with water (300 ml). The mixture was diluted in DCM, and layers were separated. Aqueous layer was extracted with DCM (3×200 ml). The combined organic layers were washed with water (2×300 ml), dried under Mg504, filtrated and concentrated. The resulting crude product was purified with a silica gel column and eluted with Cyclohexane/AcOEt (4:1) to afford to the compound (4) β CD dialdehyde per Bn (9.2 g, 88%).

The structure was not characterized by NMR but was confirmed by the reactivity of compound (4) in the following step.

Step d): Synthesis of a Capped Perbenzylated β-Cyclodextrin: Compound (5): β CD Capped (C4) Diamine Per Bn.

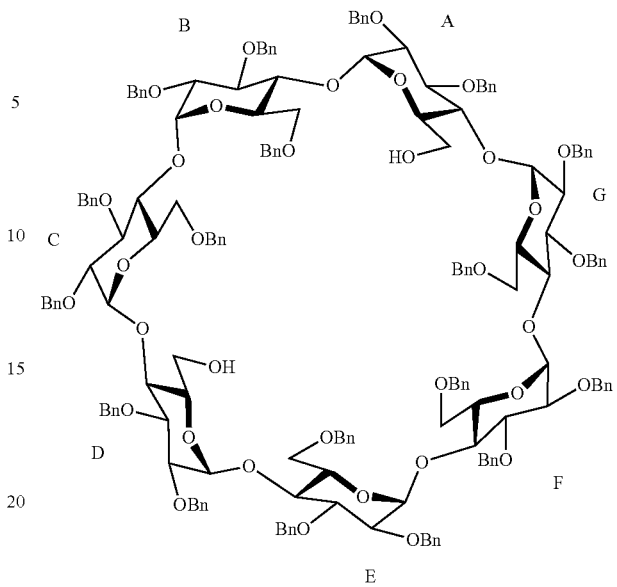

Protocol:

β CD dialdehyde per Bn (compound 4) (9.2 g, 3.24 mmol) was solubilized in DCM (100 ml). Butane-1,4-diamine (0.4 ml, 3.99 mmol) and Sodium triacetoxyborohydride (3.5 g, 16.51 mmol) were then added at rt. The solution was stirred during 1h30. EtOAc (200 ml) and $NaHCO_3$ (200 ml) were added. Layers are separated, aqueous layer is extracted with AcOEt (2×200 ml). Organic layers were combined and washed with $NaHCO_3$ and NaCl, dried with Mg504 and concentrated. The resulting crude product was purified with a silica gel column (700 ml) and eluted with Cyclohexane/AcOEt (4:1 then 6:4 with $Et_3N$) to afford compound (5) β CD bridge (C4) diamine per Bn (7.76 g, 83%).

RMN (600 MHz, $CDCl_3$):

| | | | | |
|---|---|---|---|---|
| Cycle α/G | H-1 α | 5.77 | 3.58 | $^\varphi H_4$ |
| | C-1 α | 97.88 | | |
| | H-2 α | 3.55 | | |
| | C-2 α | 78.05 | | |
| | H-3 α | 4.10 | | |
| | C-3 α | 81.00 | | |
| | H-4 α | 4.00 | 3.99 | $^\varepsilon H_1$ |
| | C-4 α | 81.49 | | |
| | H-5 α | 3.81 | | |
| | C-5 α | 71.95 | | |
| | H-6 α | 3.70 | | |
| | | 3.57 | | |
| | C-6 α | 69.13 | | |
| Cycleβ/C | H-1 β | 5.32 | 4.06 | $^\eta H^4$ |
| | C-1 β | 98.40 | | |
| | H-2 β | 3.47 | | |
| | C-2 β | 79.07 | | |
| | H-3 β | 3.99 | | |
| | C-3 β | 81.64 | | |
| | H-4 β | 3.91 | 3.92 | $^\delta H_1$ |
| | C-4 β | 80.83 | | |
| | H-5 β | 3.80 | | |
| | C-5 β | 71.64 | | |
| | H-6 β | 3.56 | | |
| | | 3.90 | | |
| | C-6 β | 69.28 | | |
| Cycleγ/D | H-1γ | 5.20 | 3.27 | $^\eta H_4$ |
| | C-1 γ | 99.29 | | |
| | H-2 γ | 3.51 | | |
| | C-2 γ | 78.96 | | |
| | H-3 γ | 4.11 | | |
| | C-3 γ | 81.31 | | |

-continued

|  |  |  |  |  |
|---|---|---|---|---|
|  | H-4 γ | 4.06 | 4.06 | $^{β}H_1$ |
|  | C-4 γ | 77.28 |  |  |
|  | H-5 γ | 3.99 |  |  |
|  | C-5 γ | 71.46 |  |  |
|  | H-6 γ | 3.63 |  |  |
|  |  | 4.09 |  |  |
|  | C-6 γ | 68.85 |  |  |
| Cycle δ/B | H-1 δ | 4.96 | 3.92 | $^{β}H_4$ |
|  | C-1 δ | 99.56 |  |  |
|  | H-2 δ | 3.44 |  |  |
|  | C-2 δ | 78.63 |  |  |
|  | H-3 δ | 3.96 |  |  |
|  | C-3 δ | 80.52 ou |  |  |
|  | H-4 δ | 3.92 | 3.91 | $^{φ}H_1$ |
|  | C-4 δ | 81.27 |  |  |
|  | H-5 δ | 3.85 |  |  |
|  | C-5 δ | 72.03 ou |  |  |
|  | H-6 δ | 4.21 |  |  |
|  |  | 3.46 |  |  |
|  | C-6 δ | 68.65 |  |  |
| Cycle ε/F | H-1 ε | 4.89 | 3.99 | $^{α}H_4$ |
|  | C-1 ε | 99.70 |  |  |
|  | H-2 ε | 3.41 |  |  |
|  | C-2 ε | 78.79 |  |  |
|  | H-3 ε | 3.98 |  |  |
|  | C-3 ε | 81.70 ou |  |  |
|  | H-4 ε | 3.81 | 3.81 | $^{η}H_1$ |
|  | C-4 ε | 81.39 |  |  |
|  | H-5 ε | 3.83 |  |  |
|  | C-5 ε | 72.05 ou |  |  |
|  | H-6 ε | 4.02 |  |  |
|  |  | 3.42 |  |  |
|  | C-6 ε | 68.54 |  |  |
| Cycle φ/A | H-1 φ | 4.73 | 3.91 | $^{δ}H_4$ |
|  | C-1 φ | 98.13 |  |  |
|  | H-2 φ | 3.31 |  |  |
|  | C-2 φ | 80.23 |  |  |
|  | H-3 φ | 3.98 |  |  |
|  | C-3 φ | 81.70 ou |  |  |
|  | H-4 φ | 3.58 | 3.58 | $^{α}H_1$ |
|  | C-4 φ | 76.11 |  |  |
|  | H-5 φ | 4.07 |  |  |
|  | C-5 φ | 69.59 |  |  |
|  | H-6 φ | 2.79 |  |  |
|  |  | 2.66 |  |  |
|  | C-6 φ | 51.36 |  |  |
| Cycle η/E | H-1 η | 4.69 | 3.81 | $^{ε}H_4$ |
|  | C-1 η | 98.92 |  |  |
|  | H-2 η | 3.27 |  |  |
|  | C-2 η | 79.80 |  |  |
|  | H-3 η | 3.96 |  |  |
|  | C-3 η | 80.52 ou |  |  |
|  | H-4 η | 3.27 | 3.27 | $^{γ}H_1$ |
|  | C-4 η | 81.91 |  |  |
|  | H-5 η | 3.91 |  |  |
|  | C-5 η | 69.72 |  |  |
|  | H-6 η | 3.04 |  |  |
|  |  | 2.50 |  |  |
|  | C-6 η | 52.70 |  |  |

Step e): Synthesis of the Perbenzylated Cyclodextrin-Adamantane Conjugate: Compound (8)

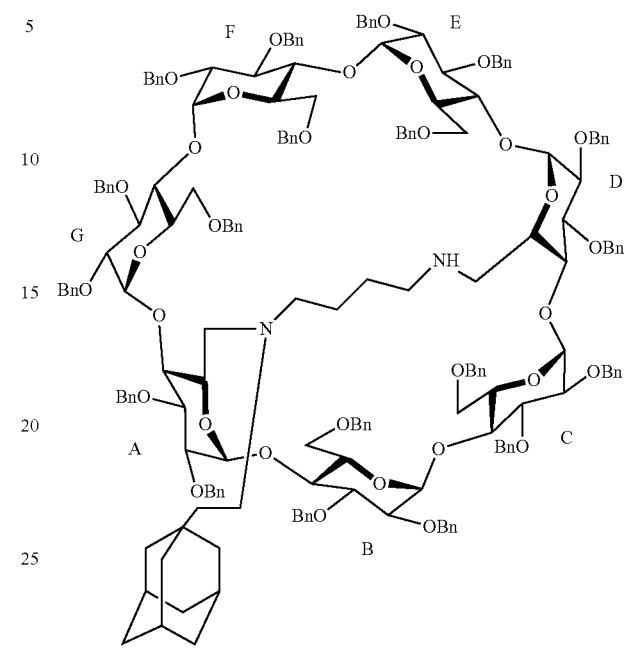

Protocol:

To a solution of β CD capped (C4) diamine per Bn (compound 5) (7.76 g, 2.68 mmol) in DCM (1200 ml) and Sodium triacétoxyborohydride (2.9 g, 13.68 mmol) was added very slowly 2-((1r,3r,5r,7r)-adamantan-2-yl)acetaldehyde (0.5 g, 2.80 mmol) at 0° C. for 1 h. Then the reaction is stirred overnight at rt. Et$_2$O (200 ml) and water (200 ml) were added, layers were separated. The Aqueous layer was extracted with Et$_2$O (2×100 ml). Organic layers were combined, washed with saturated NaHCO$_3$ and brine. The resulting crude product contained a mixture of two compounds:
- a capped perbenzylated α- or β-cyclodextrin functionalized with one adamantane group, and
- a capped perbenzylated α- or β-cyclodextrin functionalized with two adamantane group.

For obtaining the desired compound (8), the crude product was purified with a silica combi flash column (200 g) and eluted with Cyclohexane/AcOEt (gradient from 95:5 to 1:1 with Et$_3$N) to afford the expected product: β CD cap (C4) diamine mono Ad (AD) per Bn (1.86 g) and the starting material (compound 5) (4.25 g), Yield=41%.

Global Yield=21.4%.

RMN (600 MHz, CDCl$_3$):

|  |  |  |  |  |
|---|---|---|---|---|
| Cycle α/G | H-1 α | 5.66 | 3.49 | $^{η}H_1$ |
|  | C-1 α | 98.28 |  |  |
|  | H-2 α | 3.48 |  |  |
|  | C-2 α | 77.08 |  |  |
|  | H-3 α | 4.04 |  |  |
|  | C-3 α | 81.01 |  |  |
|  | H-4 α | 3.94 | 4.85 | $^{ε}H_1$ |
|  | C-4 α | 81.16 |  |  |
|  | H-5 α | 3.82 |  |  |
|  | C-5 α | 71.85 ou 72.09 |  |  |
|  | H-6 α | 4.10 |  |  |
|  |  | 3.64 |  |  |
|  | C-6 α | 69.07 |  |  |

| | | | | |
|---|---|---|---|---|
| Cycleβ/D | H-1 β | 5.26 | 3.21 | φH4 |
| | C-1 β | 99.44 | | |
| | H-2 β | 3.46 | | |
| | C-2 β | 78.72 | | |
| | H-3 β | 4.06 | | |
| | C-3 β | 81.67 | | |
| | H-4 β | 4.00 | 5.19 | δH1 |
| | C-4 β | 78.46 | | |
| | H-5 β | 3.98 | | |
| | C-5 β | 71.23 | | |
| | H-6 β | 3.60 | | |
| | | 4.10 | | |
| | C-6 β | 68.93 | | |
| Cycleγ/C | H-1 γ | 5.19 | 4.00 | βH4 |
| | C-1 γ | 98.43 | | |
| | H-2 γ | 3.39 | | |
| | C-2 γ | 79.38 | | |
| | H-3 γ | 3.90 | | |
| | C-3 γ | 80.29 ou 80.58 | | |
| | H-4 γ | 3.77 | 4.88 | δH1 |
| | C-4 γ | 81.24 ou 81.75 | | |
| | H-5 γ | 3.72 | | |
| | C-5 γ | 71.87 | | |
| | H-6 γ | 3.81 | | |
| | | 3.53 | | |
| | C-6 γ | 69.38 | | |
| Cycleδ/B | H-1 δ | 4.88 | 3.77 | γH4 |
| | C-1 δ | 100.29 | | |
| | H-2 δ | 3.33 | | |
| | C-2 δ | 78.46 | | |
| | H-3 δ | 3.90 | | |
| | C-3 δ | 80.29 ou 80.58 | | |
| | H-4 δ | 3.78 | 4.64 | ηH1 |
| | C-4 δ | 81.24 ou 81.75 | | |
| | H-5 δ | 3.80 | | |
| | C-5 δ | 71.85 ou 72.09 ou 72.18 | | |
| | H-6 δ | 3.46 | | |
| | | 4.12 | | |
| | C-6 δ | 68.93 | | |
| Cycleε/F | H-1 ε | 4.85 | 3.94 | αH4 |
| | C-1 ε | 99.38 | | |
| | H-2 ε | 3.36 | | |
| | C-2 ε | 79.52 | | |
| | H-3 ε | 3.90 | | |
| | C-3 ε | 80.29 ou 80.58 | | |
| | H-4 ε | 3.76 | 4.81 | φH1 |
| | C-4 ε | 81.24 ou 81.75 | | |
| | H-5 ε | 3.82 | | |
| | C-5 ε | 71.85 ou 72.09 ou 72.18 | | |
| | H-6 ε | 3.54 | | |
| | | 4.30 | | |
| | C-6 ε | 69.62 | | |
| Cycleφ/E | H-1 φ | 4.81 | 3.76 | εH4 |
| | C-1 φ | 99.72 | | |
| | H-2 φ | 3.23 | | |
| | C-2 φ | 79.89 | | |
| | H-3 φ | 3.95 | | |
| | C-3 φ | 80.97 | | |
| | H-4 φ | 3.21 | 5.26 | βH1 |
| | C-4 φ | 81.91 | | |
| | H-5 φ | 3.73 | | |
| | C-5 φ | 70.36 | | |
| | H-6 φ | 2.48 | | |
| | | 2.39 | | |
| | C-6 φ | 59.44 | | |
| Cycle η/A | H-1 η | 4.64 | 3.78 | δH4 |
| | C-1 η | 98.45 | | |
| | H-2 η | 3.25 | | |
| | C-2 η | 80.51 | | |
| | H-3 η | 3.92 | | |
| | C-3 η | 81.75 | | |
| | H-4 η | 3.49 | 5.66 | αH1 |
| | C-4 η | 77.47 | | |
| | H-5 η | 3.97 | | |
| | C-5 η | 69.99 | | |
| | H-6 η | 2.53 | | |
| | | 2.80 | | |
| | C-6 η | 51.85 | | |

Step f): Deprotection of the Perbenzylated Cyclodextrin Conjugate (Compound (8)) and Step e)) Exchange of the Trifluoroacetate Ions with Chlorhydrate Ions: (Compound (10))

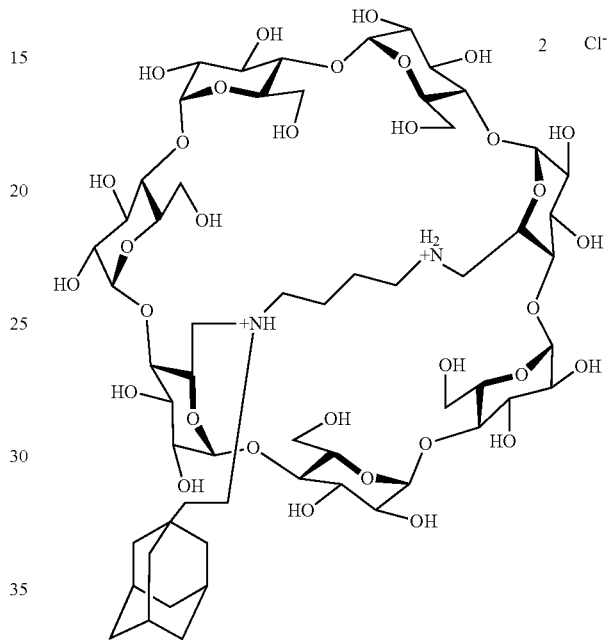

Protocol:

Compound (8) (101 mg, 0.033 mmol) was dissolved in THF/H$_2$O (18/6 ml) under argon atmosphere in a 100 ml round bottom flask. 2,2,2-trifluoroacetic acid (20 μl, 0.260 mmol) and palladium (100 mg, 0.940 mmol) were added and the reaction mixture was stirred under H$_2$ atmosphere for 24 h. Then the mixture was purged under nitrogen, filtered through a pad of celite. The organic solvents were evaporated under vacuum and the residue was lyophilized. The crude product was filtrated through a micro filter and purified by HPLC (0-40 min/0-40%/ACN:H$_2$O) to afford a white amorphous powder (24 mg, 46%). The powder was solubilized in the minimum volume of water, and eluted with water through a Ion exchange column (Amberlite Cl resin). The product is then lyophilized to afford to a powder that was solubilized in the minimum volume of water, precipitated in acetone and centrifuged. Acetone was removed. The operation was carried out twice to afford to a white solid, which was dissolved in water, and freeze dried to afford the expected product (10) as a white amorphous powder (17 mg, 32%).

RMN (600 MHz, D$_2$O):

| | | | |
|---|---|---|---|
| Cycle α | H-1 α | 5.20 | 3.79 |
| | C-1 α | 102.26 | |
| | H-2 α | 3.75 | |
| | C-2 α | | |
| | H-3 α | 3.96 | |

|  |  |  |
|---|---|---|
|  | C-3 α |  |
|  | H-4 α |  |
|  | C-4 α |  |
|  | H-5 α |  |
|  | C-5 α |  |
|  | H-6 α |  |
|  | C-6 α |  |
| Cycle β | H-1 β | 5.17 |
|  | C-1 β | 102.87 |
|  | H-2 β | 3.75 |
|  | C-2 β |  |
|  | H-3 β | 3.94 |
|  | C-3 β |  |
|  | H-4 β |  |
|  | C-4 β |  |
|  | H-5 β |  |
|  | C-5 β |  |
|  | H-6 β |  |
|  | C-6 β |  |
| Cycle γ | H-1 γ | 5.14 |
|  | C-1 γ | 102.26 |
|  | H-2 γ | 3.72 |
|  | C-2 γ |  |
|  | H-3 γ | 3.97 |
|  | C-3 γ |  |
|  | H-4 γ |  |
|  | C-4 γ |  |
|  | H-5 γ |  |
|  | C-5 γ |  |
|  | H-6 γ |  |
|  | C-6 γ |  |
| Cycle δ | H-1 δ | 5.13 |
|  | C-1 δ | 102.00 |
|  | H-2 δ | 3.68 |
|  | C-2 δ |  |
|  | H-3 δ | 3.99 |
|  | C-3 δ |  |
|  | H-4 δ |  |
|  | C-4 δ |  |
|  | H-5 δ |  |
|  | C-5 δ |  |
|  | H-6 δ |  |
|  | C-6 δ |  |
| Cycle ε | H-1 ε | 5.102 |
|  | C-1 ε | 101.68 |
|  | H-2 ε | 3.71 |
|  | C-2 ε |  |
|  | H-3 ε | 3.93 |
|  | C-3 ε |  |
|  | H-4 ε | 3.45 |
|  | C-4 ε |  |
|  | H-5 ε | 4.05 |
|  | C-5 ε |  |
|  | H-6 ε | 3.06 |
|  |  | 3.08 |
|  | C-6 ε |  |
| Cycle φ | H-1 φ | 5.09 |
|  | C-1 φ | 100.83 |
|  | H-2 φ | 3.68 |
|  | C-2 φ |  |
|  | H-3 φ | 3.95 |
|  | C-3 φ |  |
|  | H-4 φ |  |
|  | C-4 φ |  |
|  | H-5 φ |  |
|  | C-5 φ |  |
|  | H-6 φ |  |
|  | C-6 φ |  |
| Cycle η | H-1 η | 5.09 |
|  | C-1 η | 100.08 |
|  | H-2 η | 3.74 |
|  | C-2 η |  |
|  | H-3 η | 3.91 |
|  | C-3 η |  |
|  | H-4 η | 3.54 |
|  | C-4 η |  |
|  | H-5 η | 4.10 |
|  | C-5 η |  |
|  | H-6 η | 3.33 |
|  |  | 3.33 |
|  | C-6 η | 52.55 |

Example 2

A cyclodextrin-adamantane conjugate in which the cyclodextrin is an α-cyclodextrin has been manufactured as in example 1 by only using an α-cyclodextrin instead of a β-cyclodextrin.

Example 3

In this example, a supramolecular polymer has been obtained from the cyclodextrin-adamantane conjugates (10) obtained in example 1.

The monomer of cyclodextrin was first diluted in $D_2O$ at a concentration of 15.8 mM in order to carry out the NMR DOSY experiments.

Then, several dilutions of this solution have been made in order to arrive to a final concentration of 0.079 mM.

Water is the solvent in which a supramolecular polymer can be formed since cyclodextrins can form inclusion complex in this solvent only.

$D_2O$ has the same properties as water.

Aqueous solution can also be used, of course.

In the DOSY analysis one can see that the size of the formed supramolecular polymer is more important than with the monomer. The above is true for all the tested concentrations.

However, from a concentration of 5 mM a clear raised of the diffusion coefficient is observed.

The formation of the supramolecular polymer has been demonstrated by NMR DOSY.

In this study, three compounds were studied.

compound 10 obtained in example 1, which is a capped cyclodextrin-adamantane conjugate according to the invention, the cycicodextrin-adamantane conjugate described in the article "Cyclodextrin-adamantane conjugates, self-inclusion and aggregation versus supramolecular polymer formation", *Org. Chem. Front.* 2014, 1, 703-706. This conjugate is made of a β-cyclodextrin functionalized with an adamantane group. But the cyclodextrin group is not capped. It has been demonstrated in the article "Cyclodextrin-adamantane conjugates, self-inclusion and aggregation versus supramolecular polymer formation" that this conjugate does not form a supramolecular polymer because the adamantane self-includes in the cavity of the cyclodextrin on which it is bound, the capped cyclodextrin with the formula I-1

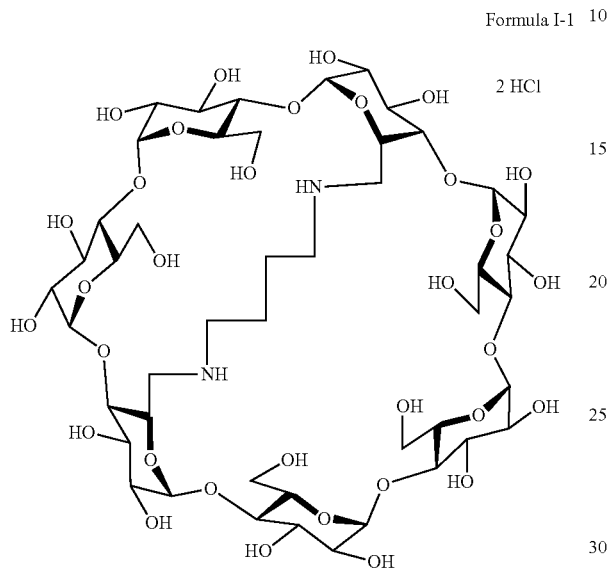

Formula I-1

2 HCl

The results of the NMR DOSY study of this example are that the diffusion coefficient of the compound functionalized with an adamantane group but in which the cyclodextrin is not capped does not vary as a function of its concentration, this being the confirmation of the fact that it does not form a supramolecular polymer.

In the same manner, the diffusion coefficient of the capped cyclodextrin not functionalized with an adamantane group does not vary as a function of its concentration. This confirms that this compound cannot form a supramolecular polymer because not having an adamantane group.

In contrast, the NMR DOSY study of the conjugate (compound 10 of example 1) of the invention shows a variation of the diffusion coefficient as a function of its concentration.

Indeed, at high concentration (15.8 mM) a diffusion coefficient higher than at low concentration (0.079 mM) is seen, confirming that the conjugate of the invention forms species having more important sizes at high concentration.

The inclusion of compound 10 obtained in example 1 in the cavity of the cyclodextrin of an other compound 10 of the invention has been demonstrated by ROESY (Rotating Frame OverHause Effect Spectroscopy) NMR study.

The ROESY NMR spectrum of the conjugate obtained in example 1 is shown in FIG. 1.

This spectrum is difficult to read due to the presence of the $CH_2$ of the linker(cap) under the signal of the H of the adamantane.

Nevertheless, it is possible to see that the adamantane group is included in the cavity of the cyclodextrin group due to the correlation of the H-3s of the cyclodextrin and the Ha and Hb of the adamantane and even in very clear manner with the two H5s of the adamantane.

But no correlation is seen between the H-5s and the protons of the adamantane which means that the adamantane is included in the cavity of the cyclodextrin. Because the self-inclusion of the adamantane in the cavity of the cyclodextrin to which it is bound is impossible due to the the capping of the cyclodextrin cavity, the adamantane group which is included in the cavity of the cyclodextrin group is indeed the adamantane group of an other cyclodextrin-adamantane conjugate.

For reinforcing this demonstration, the ROESY NMR analysis of the cyclodextrin functionalized with an adamantane group in position A of its primary rim but not capped has been made.

Figure 2:
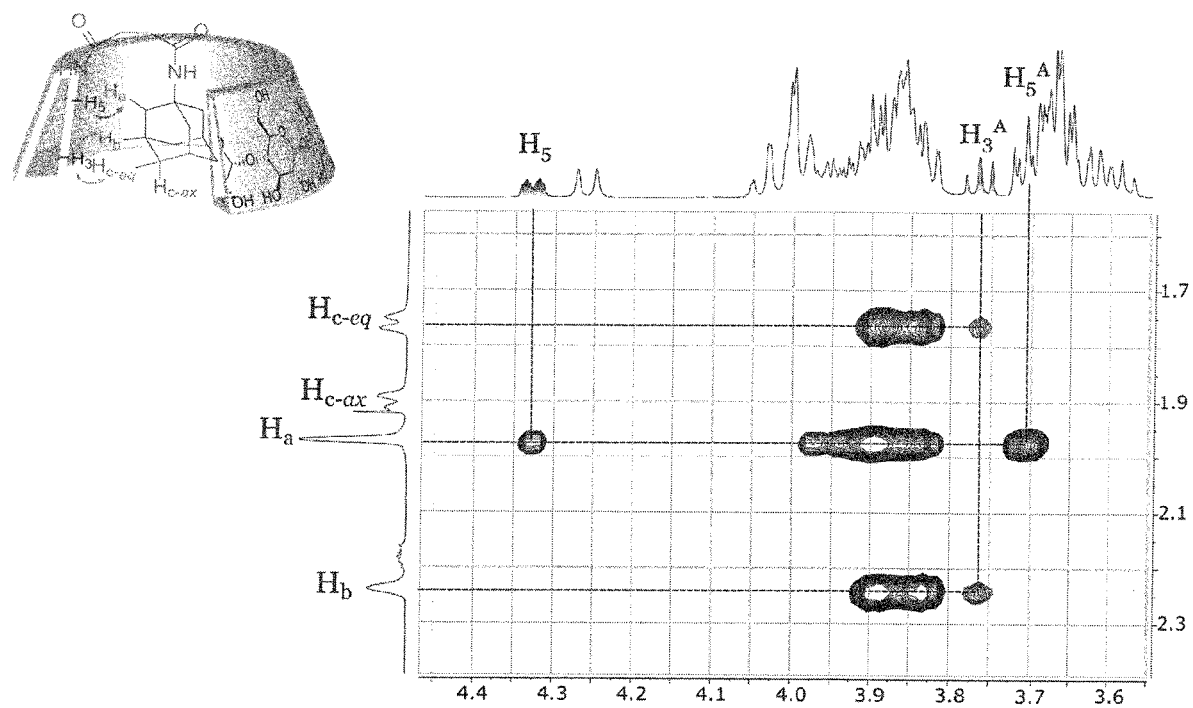
FIG. 2 shows the ROESY spectrum of a cyclodextrin group functionalized with an adamantane group but in which the cyclodextrin group is not capped.

The ROESY spectrum of this compound is shown in FIG. 2.

As can be seen in FIG. 2, in this compound the adamantane group is indeed included in the cavity of the cyclodextrin, but upside down.

Indeed, the 2D spectrum obtained with this analysis clearly shows a correlation between the H-5s of the cyclodextrin and the Ha of the adamantane while the H-3s of the cyclodextrin correlate with the Hb and Hc of the adamantane.

Example 4: Preparation of the Compound of Formula I-26

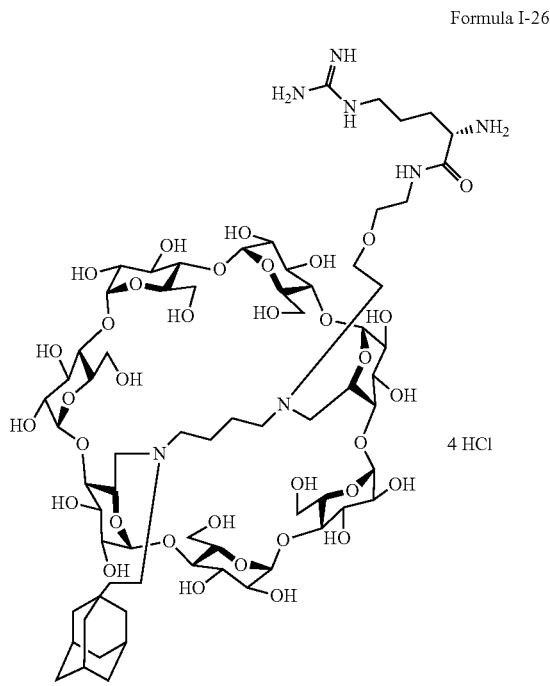

Formula I-26

4 HCl

This compound is prepared according to the following synthesis scheme.

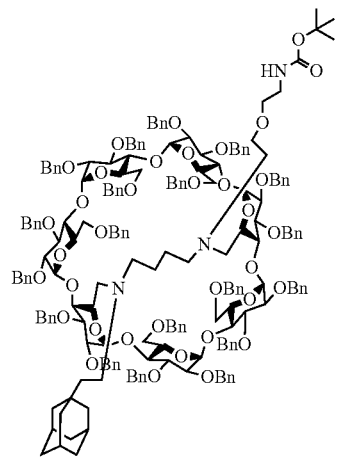

1
Chemical Formula: C$_{200}$H$_{227}$N$_3$O$_{36}$
Molecular Weight: 3249,00

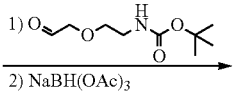

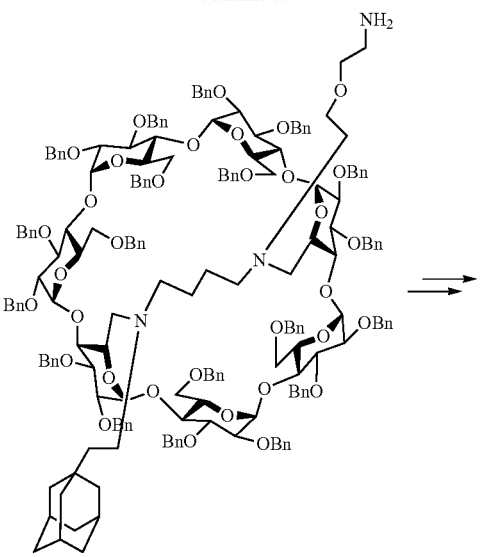

3
Chemical Formula: C$_{195}$H$_{219}$N$_3$O$_{34}$
Molecular Weight: 3148,88

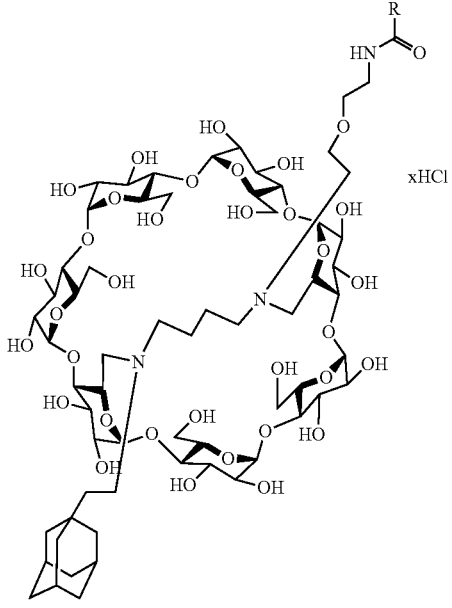

4

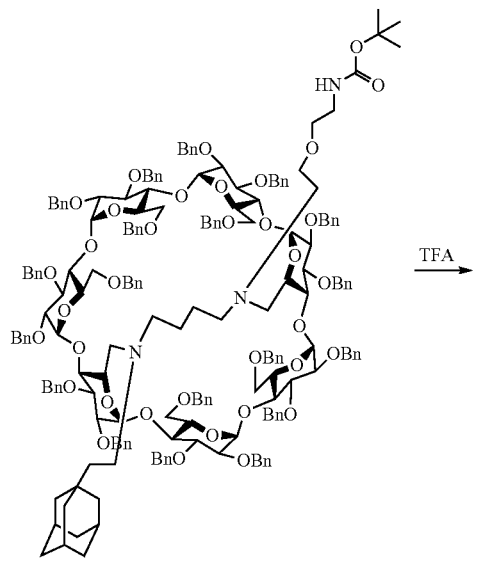

2
Chemical Formula: C$_{200}$H$_{227}$N$_3$O$_{36}$
Molecular Weight: 3249,00

For obtaining the compound of Formula I-26, noted 4 in the above synthesis scheme, in which R is NH$_2$—C=NH—NH—(CH$_2$)$_3$—CH—NH$_2$, a reductive amination is first carried out on compound 1 which is a perbenzylated capped betacyclodextrin in order to obtain compound noted 2 in the above synthesis scheme. The protective group Boc of the amine group of the second linker is then removed in an acidic medium in order to obtain a NH$_2$ group thereby obtaining compound noted 3 in the above synthesis scheme. The amine group then enables the functionalization of compound 3 via a peptidic coupling with carboxylic acids. Compound 4 is obtained by carrying out the removal of the protecting groups of Compound 4 in which R is NH$_2$—C=NH—NH—(CH$_2$)$_3$—CH—NH$_2$ i.e. the compound of Formula I-26

Example 5: Preparation of a Cyclodextrin-siRNA Complex

Compound 11 obtained in example 1 is treated in a DMEM medium (Dubelccos's modified Eagle's medium), SVF (Stromal Vascular Fraction) 10%, without antibiotics.

Then it is incubated during five minutes at ambient temperature.

The siRNAs are treated in a Opti-MEM medium SVF (poor in a fetal veal serum) and then incubated during 5 minutes at ambient temperature.

Two amounts of siRNA have been prepared: 5 pmol and 10 pmol.

Each solution of siRNA are then mixed with a solution of compound 10 and complexed during 20 minutes at ambient temperature.

Different ratio nitrogen/phosphate (NIP) of cyclodextrin-siRNA have been chosen varying from 6 to 1190.

Example 6: Comparative Example: Preparation of a Lipofectamine 2000.siRNA Complexes A Lipofectamine 2000.siRNA complexes have been prepared as follows.

These complexes are used as positive references of transfection of RNA.

Lipofectamine 2000 (Invitrogen) treated in a DMEM, SVF 10%, medium, without antibiotics and the incubated during 5 minutes at ambient temperature.

The siRNAs are treated in a Opti-MEM poor in a fetal veal serum medium and then incubated during 5 minutes at ambient temperature.

Two amounts of siRNA were prepared: 5 pmol and 10 pmol.

The solutions of siRNA and of Lipofectamine are then mixed and complexed during 20 minutes at ambient temperature: 50 µL of Lipofectamine are combined to 50 µL of siRNA.

The cell line to be transfected is a cell line of human embryonic kidney 293 cells (HEK293). This cell line is cultivated with a DMEM medium to which SVF (10%) is added.

The antibiotics penicillin and streptomycin as well as the antibiotic hygromycin B are also added.

The cultures are made in an incubator at 37° C., 5% of $CO_2$. The cell line HEK293 express constitutively the firefly luciferase GL3.

The HEK293 cells are deposited in a 96 wells plaque $1·10^3$ cell/wells.

The siRNA which is used is the luciferase GL3 siRNA.

The siRNA corresponding to the firefly luciferase issued from plasmid PGL3-basic (Promega) has been synthesized by Sigma.

The sequence indicated is under the form of an RNA (19nt) to which is added 2T in 3'(dTdT—d for deoxy—DNA).

The sequences are:

```
(sense strand)
5'-CUUACGCUGAGUACUUCGAdTdT-3'

(antisense strand)
5'-UCGAAGUACUCAGCGUAAGdTdT-3'
```

Example 7: KnockDown Test of the Luciferase GL3 Gene

Transfection of cell line HEK293 with the siRNA directed against the firefly luciferase GL3 with as vector of transfection the compound 10 obtained in example 1 or Lipofectamine 2000 (used as a positive reference of transfection) has been carried out.

The efficacy of transfection on the cells has been evaluated by a method of luminescence.

One day before the transfection, the HEK293 cells are deposited in a 96 wells plaque: $1·10^3$ cell/wells treated in 200 µL of DMEM, SVF 10%, without antibiotics, in order that the cells reach a 30-50% of confluence the day after.

The day of the transfection, the 200 µL/wells of medium are withdrawn.

After preparation of the complex of cyclodextrin-siRNA according to the invention and of Lipofectamine 2000-siRNA, 100 µL/wells of solution of siRNA-cyclodextrin of the invention or 100 µL/wells of solution of siRNA Lipofectamine 2000 are deposited in the plaque.

This latter is incubated at 37° C. during 24 hours until the analysis by luminescence of the KD of the gene of the luciferase (Kit One-Glo luciferase assay (Promega)).

For this aim, 100 µL/wells of reactants are added to the cells before the plaque be analyzed by luminescence.

Toxicity Test

In order to evaluate the toxicity of compound 11 of example 1 on HEK293 cells, the kit CellTiter Glo 2.0 (Promega) has been used.

One day before the transfection, the cells HEK293 are deposited in a 96-wells plaque: $1·10^3$ cell/wells and then treated with 200 µL of DMEM, SVF 10%, without antibiotics, in order that the cells reach a 30-50% of confluence the day after.

The day of the transfection, the cells are incubated with the complex siRNA-cyclodextrin conjugate obtained in example 1 and Lipofectamine 2000.siRNA at 37° C. during 24 hours until analysis of the cells viability (ATP activity) using a kit CellTiter Glo 2.0.

For this aim 100 µL/wells of CellTiter Glo 2.0. reactant are added to the cells before the plaque be analyzed by luminescence.

Agarose Gel Electrophorese

In order to characterize the formation of complexes between the siRNA and the compound 11 of the invention obtained in example 1, an electrophorese technique on agarose gel has been used.

The molecule of siRNA and of compound of example 1 have been migrated according to N/P previously chosen.

A solution of 17 µL of siRNA-compound of example 1 is prepared in sterile water and incubated during 20 minutes at ambient temperature.

Then, this solution is deposited on the gel with 3 µL of bromophenol blue before launching the migration: 100 V, 40 min.

One can conclude from these experiments that, thanks to ROESY-NMR studies, it has been shown that the capping of the cyclodextrin derivative avoid the self inclusion of the hydrophobic moiety. Secondly, thanks to DOSY-NMR studies, it has been shown that both the capping and the functionalization of the cyclodextrine derivative are essential to obtain results which are in agreement with the formation of supramolecular polymer.

Figure 3:
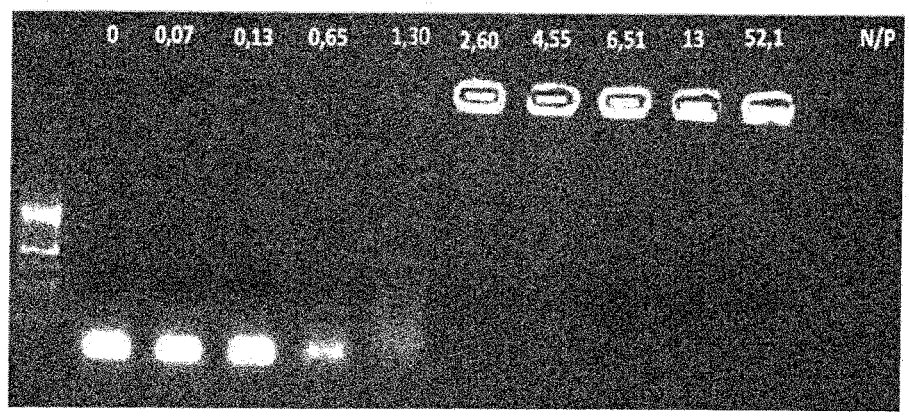
FIG. 3 shows the agarose electrophoresis gel of an increasing N/P ratio of the supramolecular polymer obtained in example 3 in the presence of siRNA as described in example 7.

Third, thanks to the experiment with agarose electrophoresis gel, it has been shown that capped cyclodextrine-adamantane conjugate are able to interact and to complex siRNA. Indeed, capped cyclodextrine-adamantane complex formation was evaluated at increasing N/P ratios using agarose gel electrophoresis. (FIG. 3)

N/P ratio corresponds to the amount of protonated aminated residue of the cationic species divided by the amount of phosphate residues coming from the nucleic acids.[14] This ratio enables to compare the efficiency of a cationic compound to be complexed with nucleic acids.

[14] Pharmaceutics. 2011, 3, 125-140

$$\text{Thus, } \frac{N}{P} = \frac{\text{number of all cationic compounds} \cdot \text{number of charges by molecule}}{\text{number of moles of } siRNA \cdot \text{number of base pairs} \times 2}.$$

In the present case, the cationic compound is a conjugate according to the invention, the number of charges by molecule is the number of charge by conjugate of the invention and the number of base pairs is the number of base pairs of the siRNA.

The positive charges of the amine group in the capped cyclodextrine-adamantane conjugate have the ability to associate with the negatively charged phosphate groups of the siRNA. While uncomplexed siRNA migrated freely through the gel, complete binding of siRNA with capped-cyclodextrine-adamantane conjugate appeared to occur abruptly at low N/P ratios, with no migration of siRNA. These results demonstrate that the negatively charged siRNA had been effectively complexed by the capped-cyclodextrine-adamantane conjugate.

Figure 4:
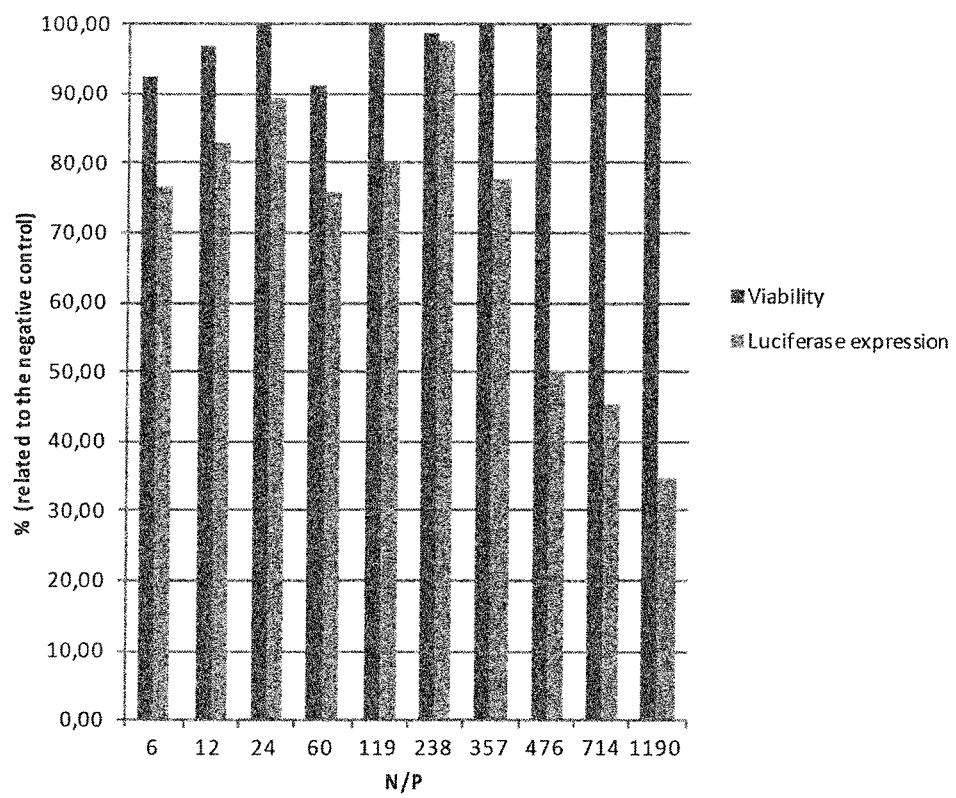
FIG. 4 shows the viability of the cells and the transfection efficiency after treatment by an increasing N/P ratio of the supramolecular polymer obtained in example 3 in the presence of siRNA as described in example 7.
Figure 5:
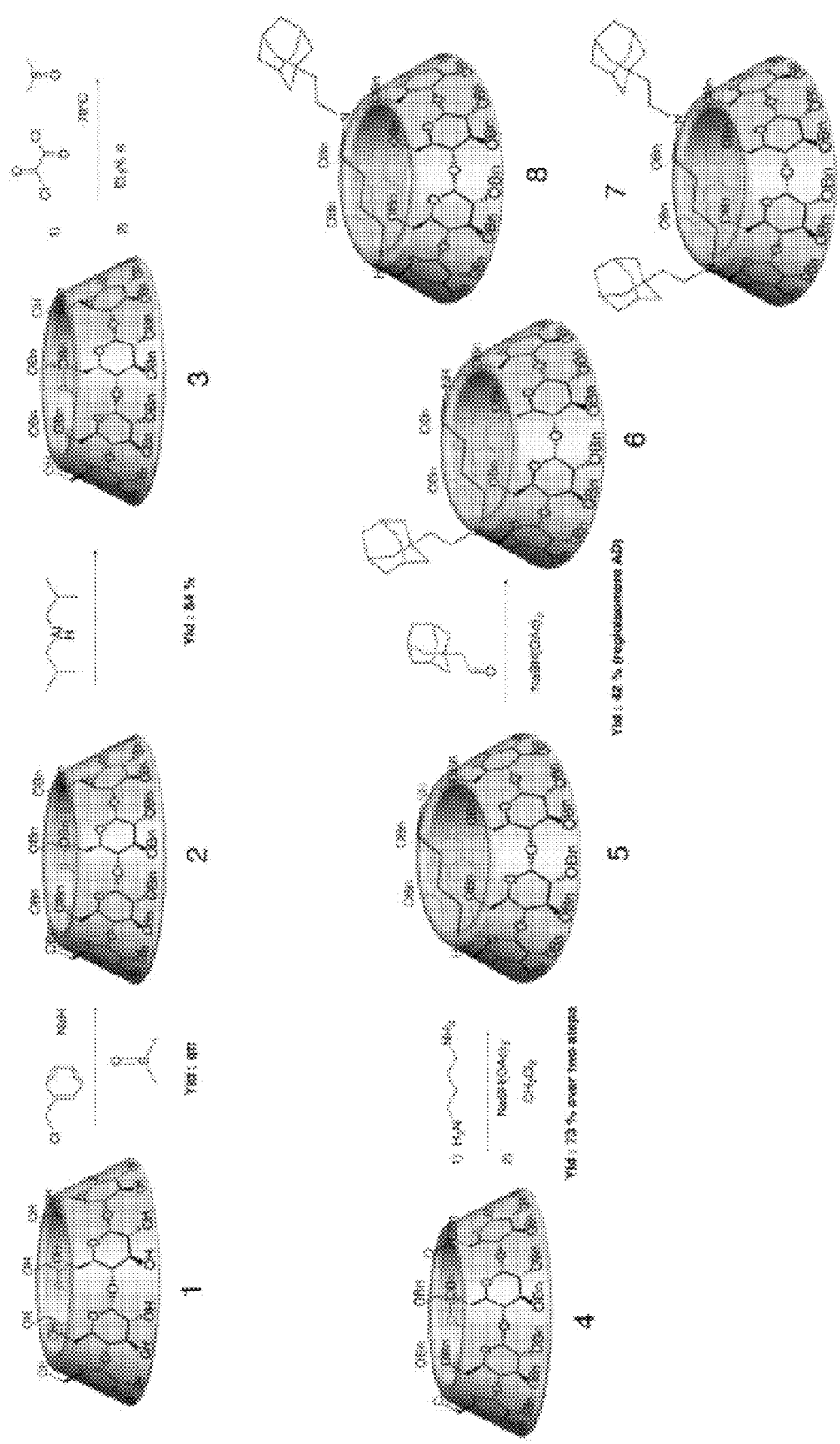
FIG. 5 shows a synthesis scheme for synthesis of a conjugate in which the cyclodextrin group is a β-cyclodextrin group in accordance with example 1.
Figure 5:
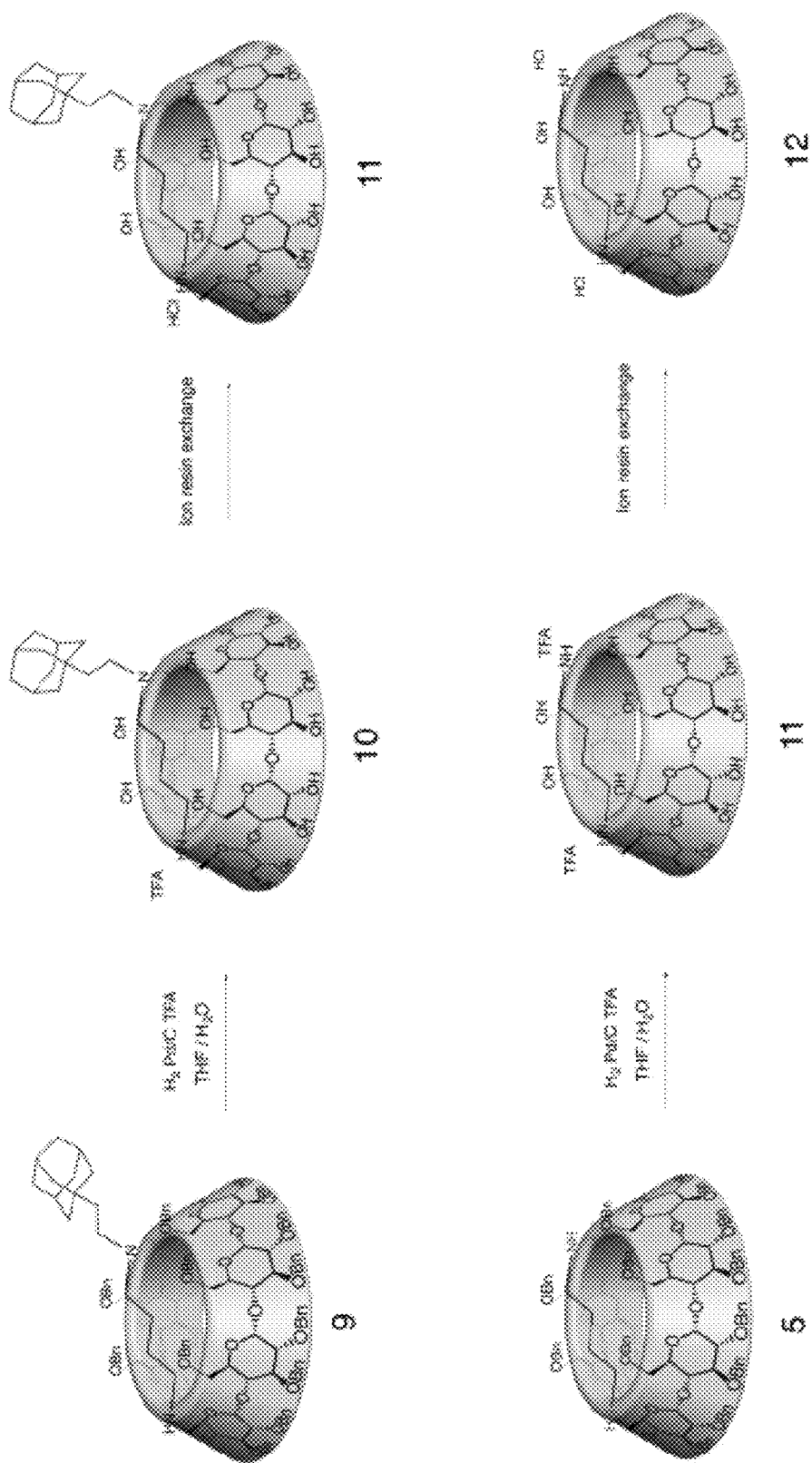
Figure 7:
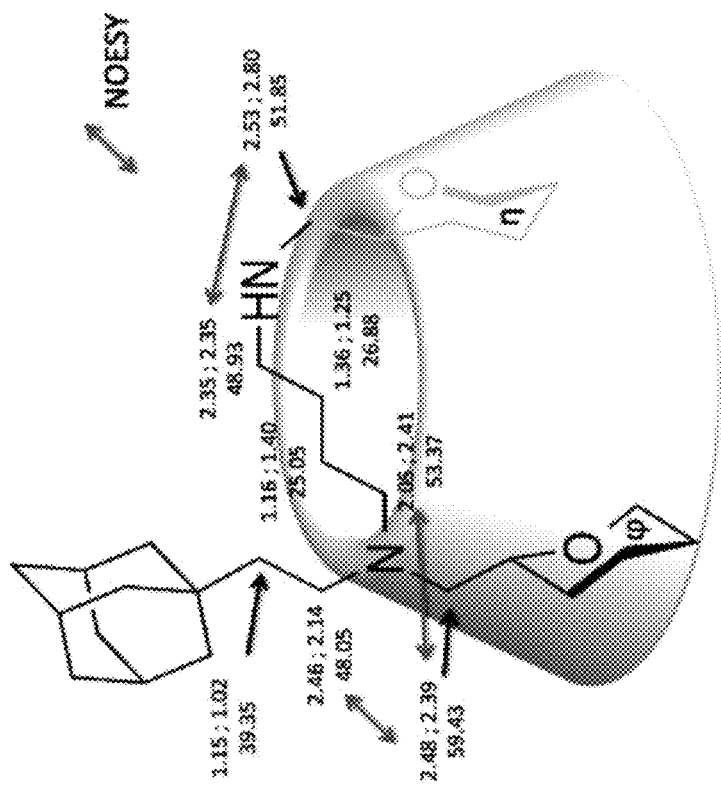
FIG. 7 shows a perbenzylated cyclodextrin-adamantane conjugate obtained in step e of example 1.
Figure 6:
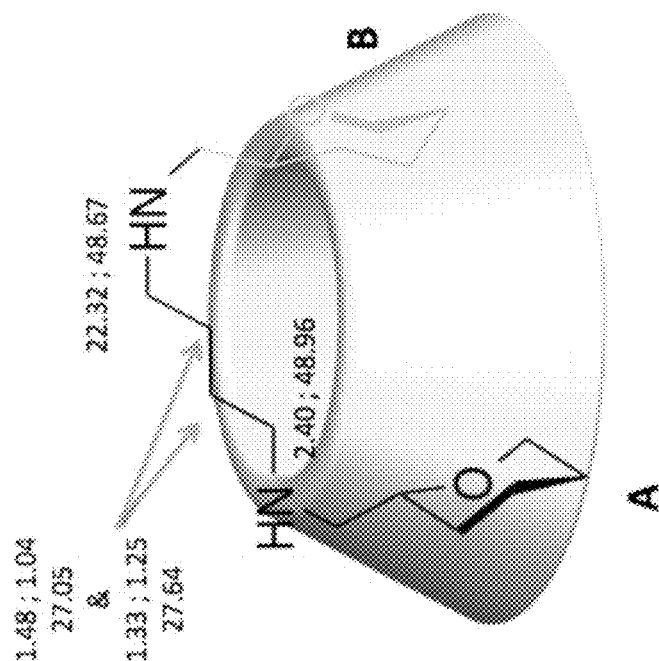
FIG. 6 shows a capped perbenzylated β-cyclodextrin obtained in step d of example 1.

Finally, the results of transfection also showed the capacity of the capped cyclodextrine-adamantane conjugate to transfect siRNA. The in vitro transfection activity of capped cyclodextrine-adamantane vector was evaluated in HEK293 cells at a range of N/P ratios. The HEK293 cells have a constitutive expression of the firefly luciferase (GL3). Untransfected cells was considered as 100% of luciferase expression (negative control). A reduction in GL3 luciferase expression was achieved with transfection in HEK293 cells with the capped cyclodextrine-adamantane siRNA complexes (compose 11). In fact, until 50% knockdown was observed for a transfection at the N/P ratio of 1190. These transfection efficiencies are lower than that of lipofectamine 2000 (knockdown of 90%). Nevertheless, over the range of N/P ratios, transfection with capped cyclodextrine-adamantane siRNA complexes exhibited no cytotoxicity. Overall, these tests showed the ability of capped-cyclodextrine-adamantane (compose 11) to transfect siRNA in HEK293 cells with a favorable toxicity profile. (FIG. 4)

The invention claimed is:

1. A capped cyclodextrin-hydrophobic moiety conjugate comprising a cyclodextrin moiety and at least one hydrophobic moiety, wherein:

the cyclodextrin moiety is capped on its primary rim by a cap binding a first carbon atom, previously bearing a hydroxyl group, of a first glucopyranose unit to a second carbon, previously bearing an hydroxyl group, of a second and different glucopyranose unit, said first and second glucopyranose units being preferably separated from each other by at least one, and the hydrophobic moiety is bound by a first linker to one of the carbon atoms of the cap, and the hydrophobic moiety is selected from the group consisting of an adamantane group, a $C_2$-$C_{13}$ alkyl group optionally containing at least one heteroatom, a $C_5$-$C_6$ aromatic group optionally containing at least one heteroatom and a $C_3$-$C_8$ non-aromatic cycle optionally containing at least one heteroatom.

2. The capped cyclodextrin-hydrophobic moiety conjugate according to claim 1, wherein the hydrophobic moiety is selected from the group consisting of an adamantane group and a phenyl group.

3. The capped cyclodextrin-hydrophobic moiety conjugate of claim 1, wherein:
said cap and said first linker, independently from each other, form, together with the carbon atoms to which they are bound, a chain having from 2 to 20 links,
said chain comprising at least one heteroatom chosen in the group consisting of N, O, S and P and/or at least one functional group selected from the group consisting of a ketone group, an amine group, an ether group, an amide group, an ester group, a cyano group, and optionally comprising a non: aromatic or aromatic cyclic or heterocyclic group having from 3 to 8 links.

4. The capped cyclodextrin-hydrophobic moiety conjugate of claim 1, wherein the cyclodextrin moiety is an α- or β-cyclodextrin moiety.

5. The capped cyclodextrin-hydrophobic moiety conjugate of claim 1, wherein the cap binds the carbon atoms, previously bearing a hydroxyl group, in position 6 of the glucopyranose units, the glucopyranose units being in position A and D of the primary rim of the cyclodextrin moiety.

6. The capped cyclodextrin-hydrophobic moiety conjugate according to claim 1, wherein the cap comprises a first heteroatom and wherein the hydrophobic moiety is bound to this first heteroatom.

7. The capped cyclodextrin-hydrophobic moiety conjugate according to claim 6, wherein the cap comprises a second heteroatom which either form a positively charged link of the cap or to which at least one positively charged group is bound, the positively charged group being selected from the group consisting of a primary amine group, a secondary amine group, a guanidinium group and combination thereof.

8. The capped cyclodextrin-hydrophobic moiety conjugate of claim 7, wherein said first and second heteroatom are nitrogen atoms.

9. The capped cyclodextrin-hydrophobic moiety conjugate according to claim 1 having one of the following formulae I-1 to I-26:

Formula I-1

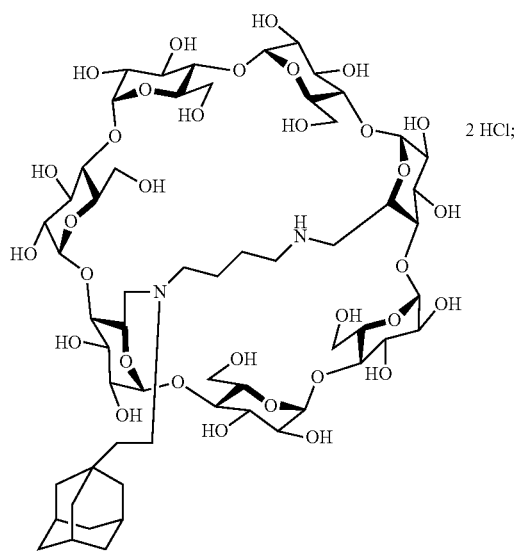

Formula I-2

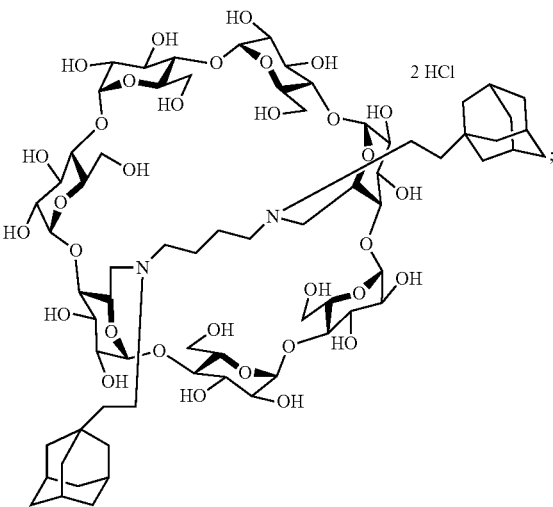

Formula I-3

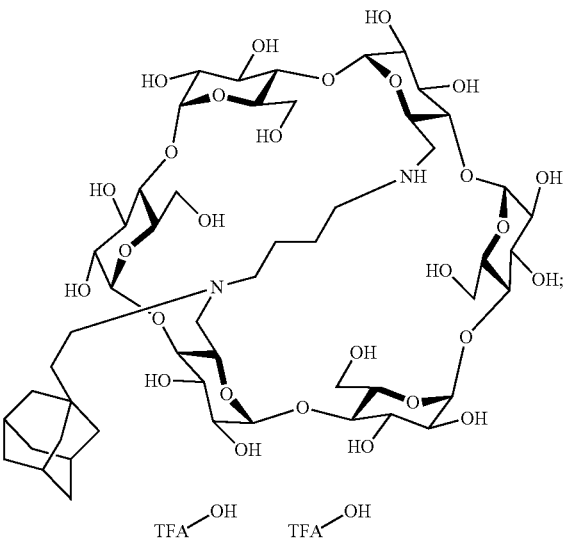

Formula I-4

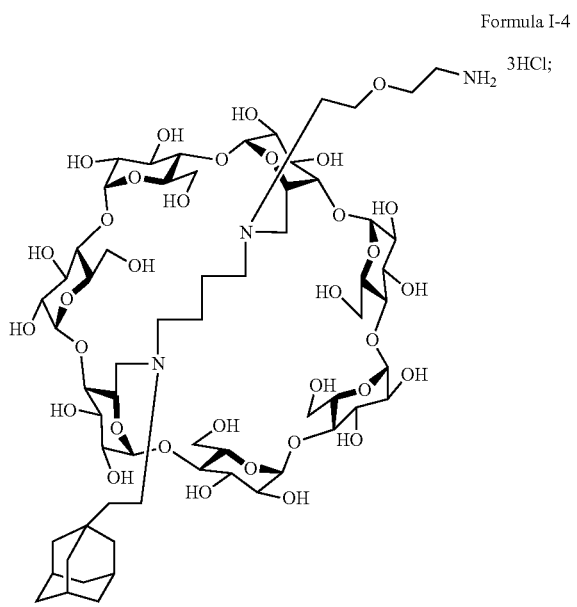

Formula I-5

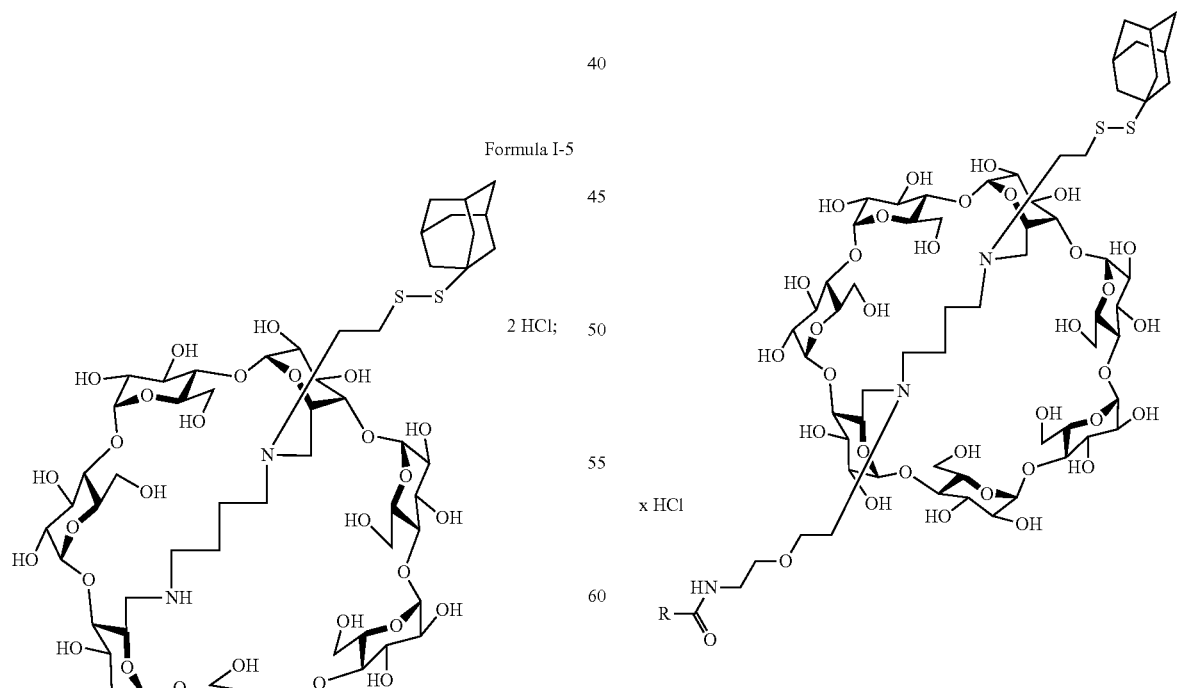

Formula I-6

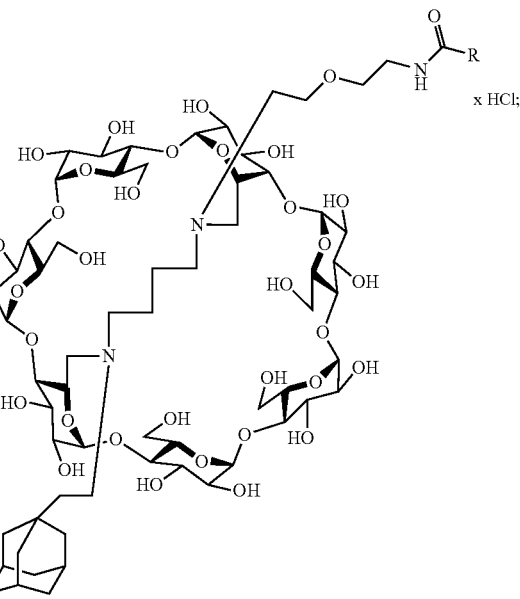

in which R is an amine group, an arginine group, a guanidine group, or a linear or branched chain comprising between 1 and 20 atoms for the main chain, these atoms being nitrogen atoms and/or oxygen atoms and/or carbon atoms, such a chain optionally comprising from 1 to 30 amine groups or guanidine groups, and in which x is equal to the number of amine group(s) plus the number of guanidine group(s) in R;

Formula I-7 in which R is an amine group, an arginine group, a guanidine group, or a linear or branched chain comprising between 1 and 20 atoms for the main chain, these atoms being nitrogen atoms and/or -oxygen atoms and/or carbon atoms, such a chain optionally comprising from 1 to 30 amine groups or guanidine groups, and in which x is equal to the number of amine group(s) plus the number of guanidine group(s) in R;
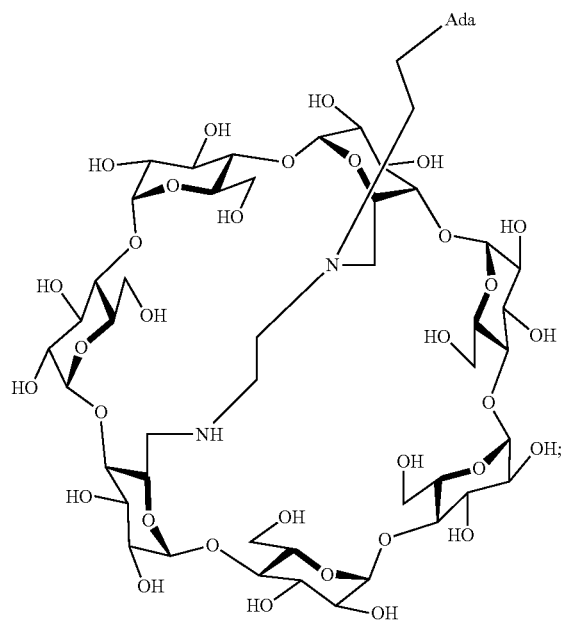
Formula I-8
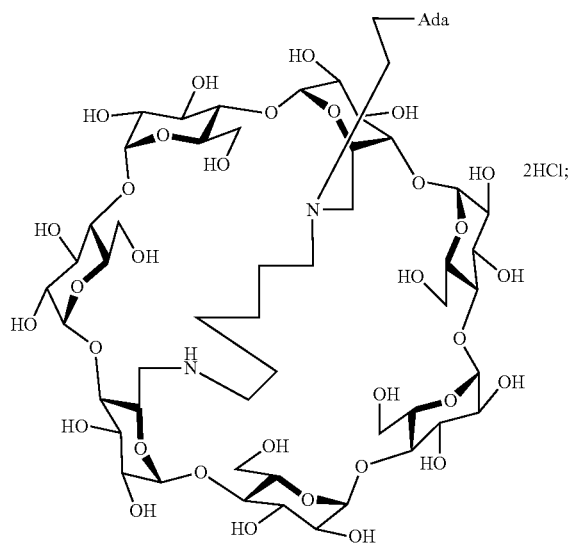
Formula I-9
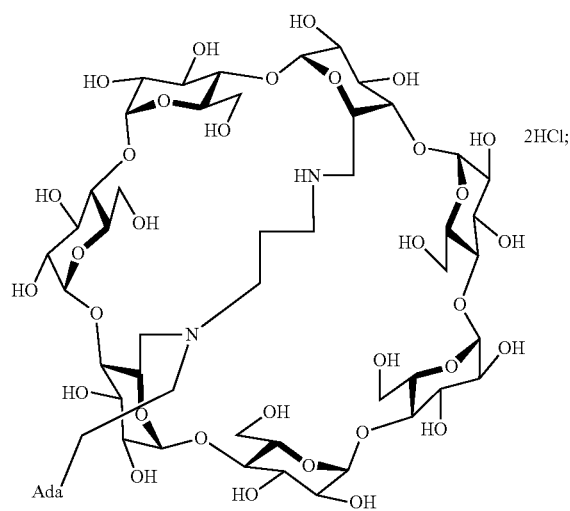
Formula I-10
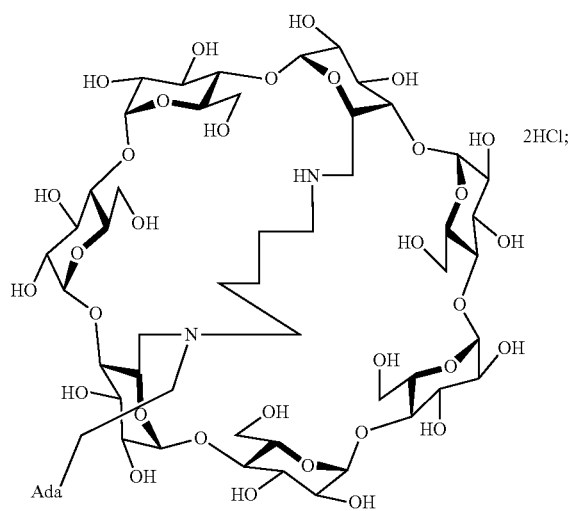
Formula I-11

Formula I-12
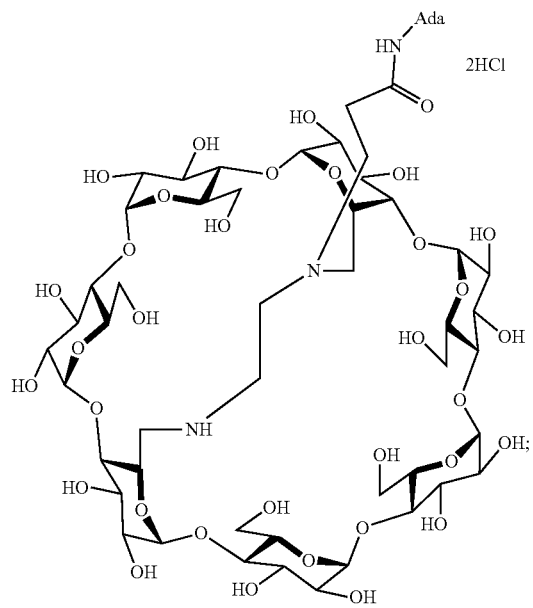
Formula I-13
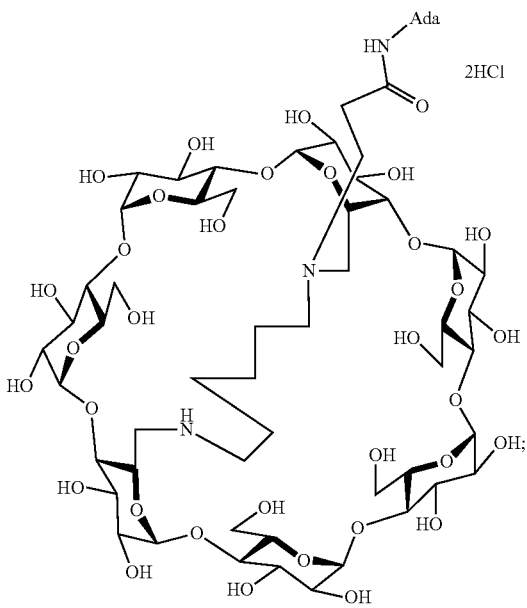
Formula I-14
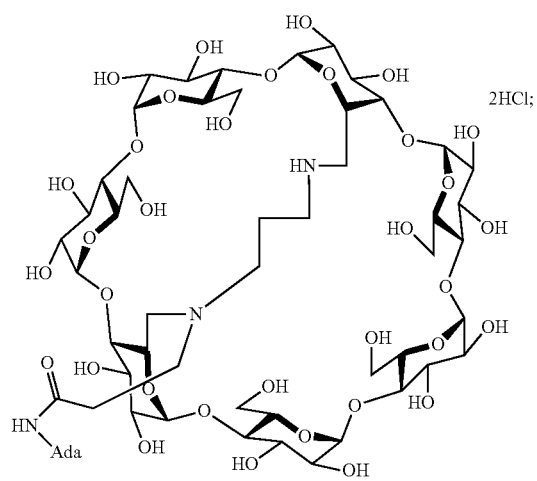
Formula I-15
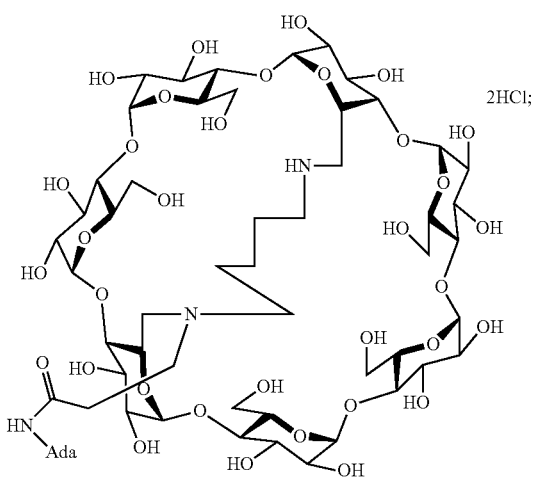
Formula I-16
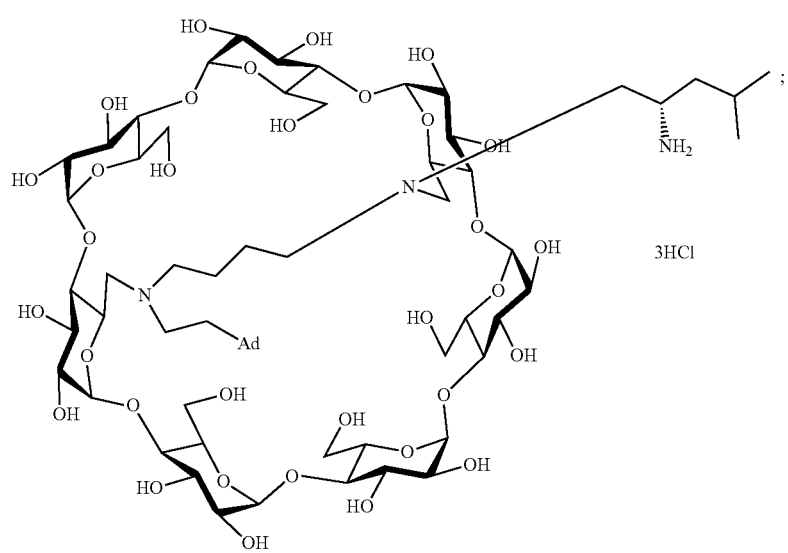

Formula I-17
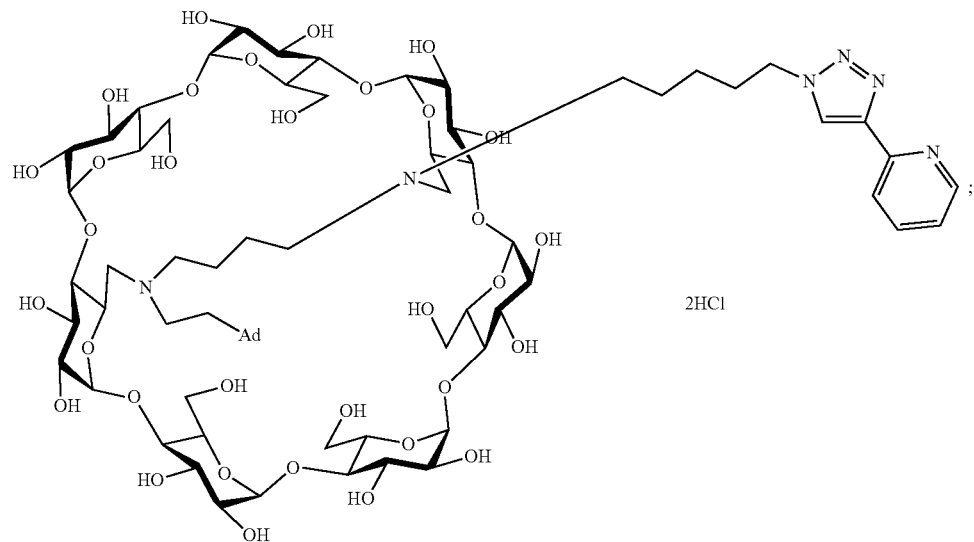
Formula I-18
Formula I-19
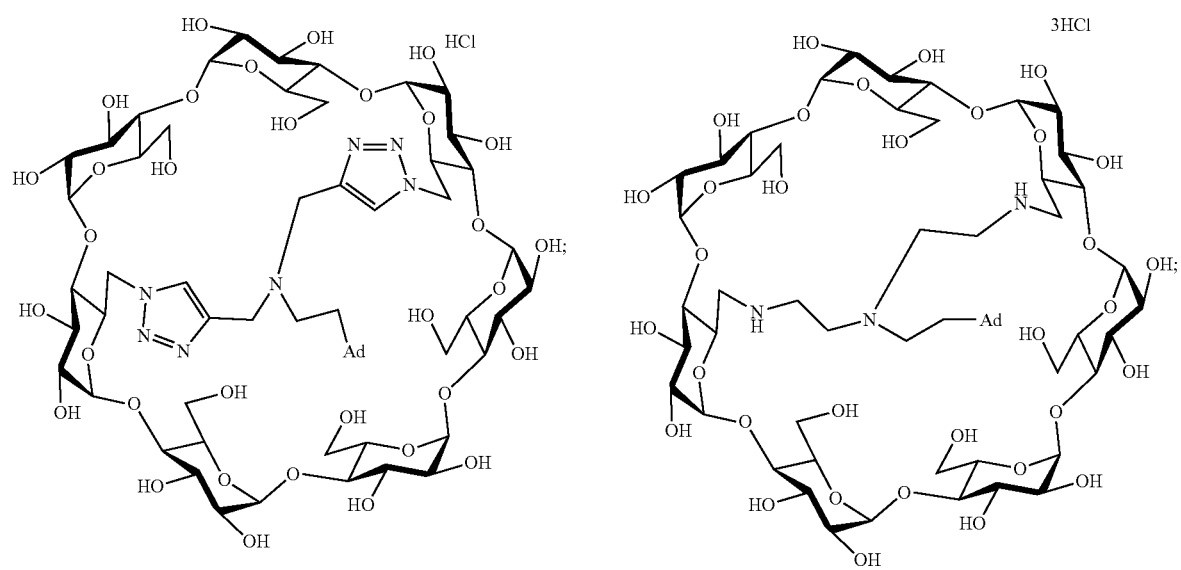
Formula I-20
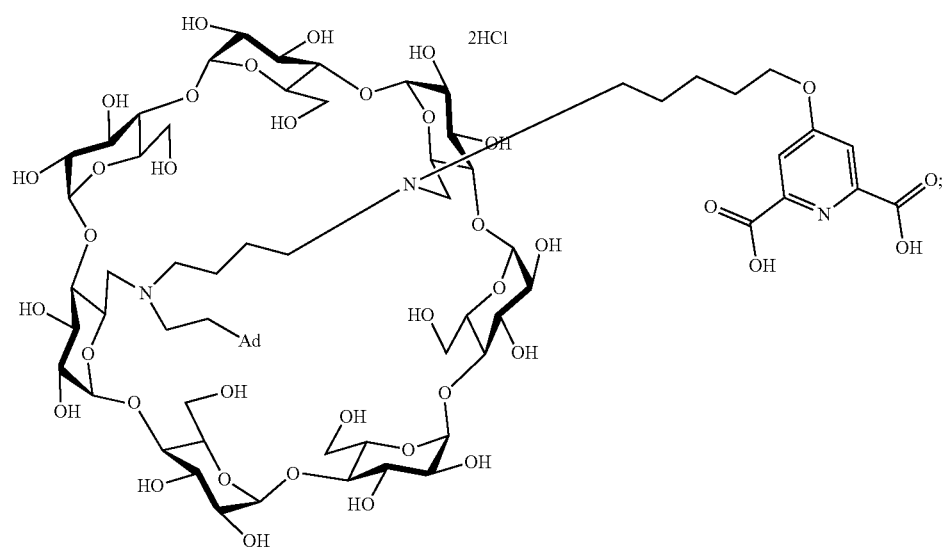

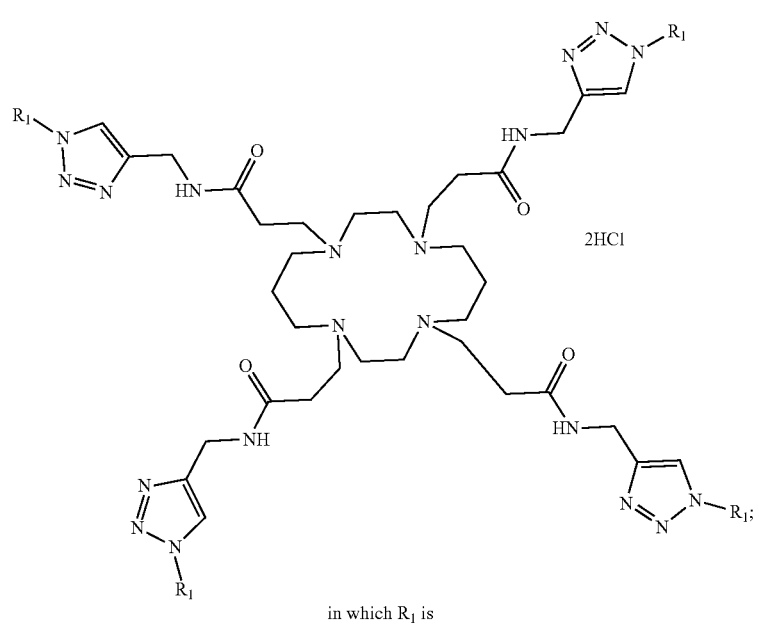
Formula I-21
in which $R_1$ is
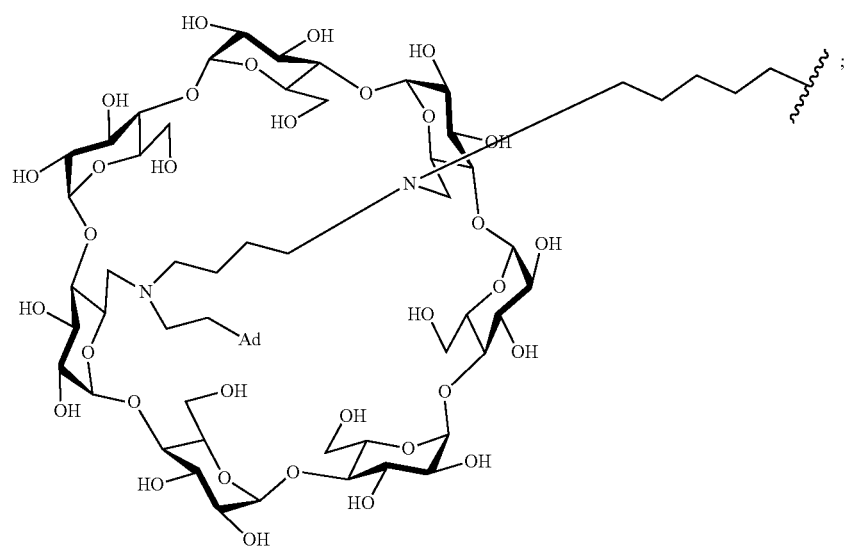

Formula I-22
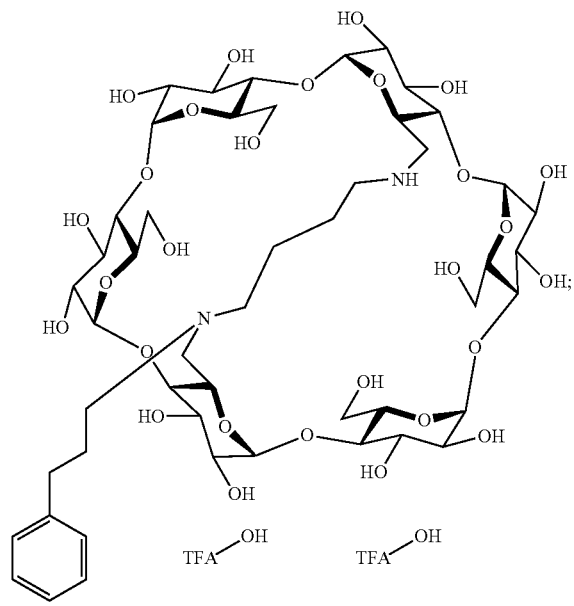
Formula I-23
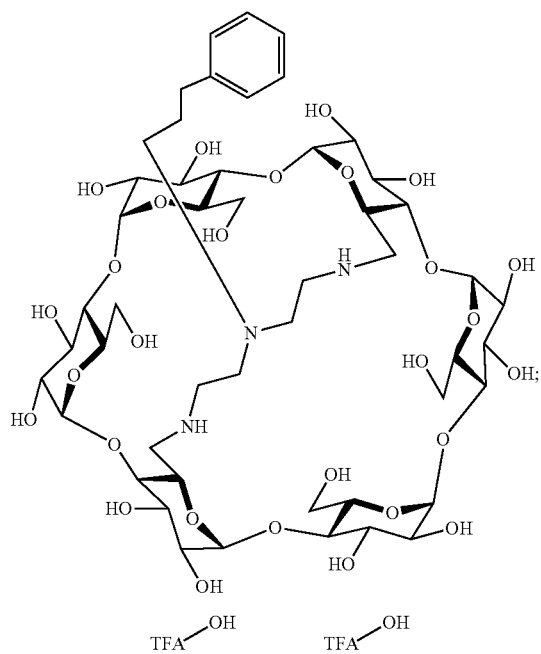
Formula I-24
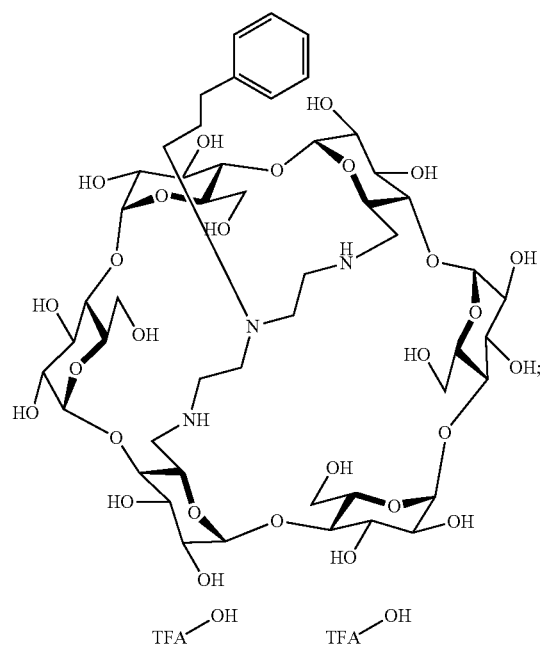

-continued
Formula I-25
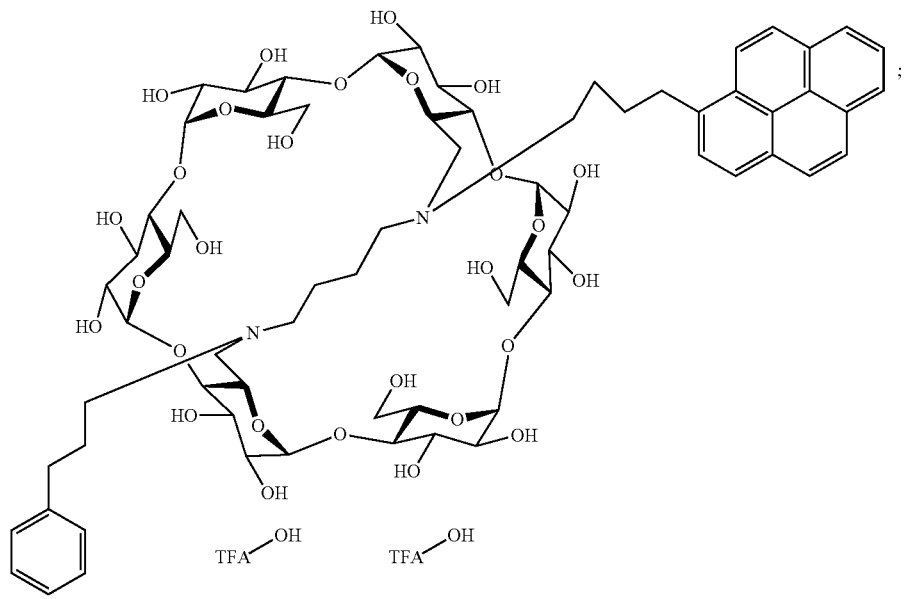
Formula I-26
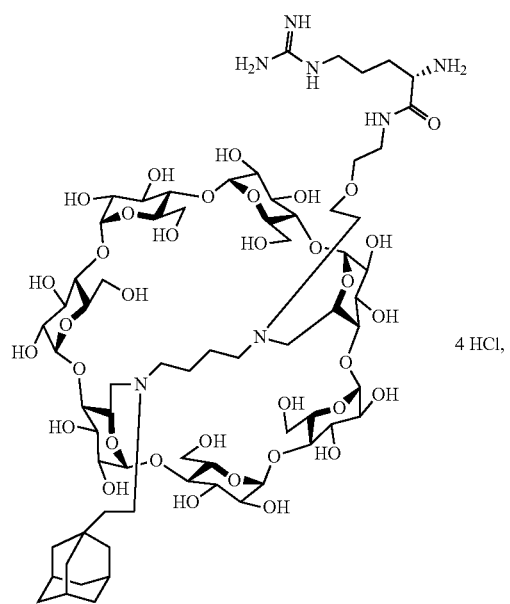

wherein in formulas I-4 to I-11, "Ada" designates an adamantane group and in formulas I-12 to I-17, "Ad" designates an adamantane group.

10. The capped cyclodextrin-hydrophobic moiety conjugate according to claim 1 having the following formula I-1:

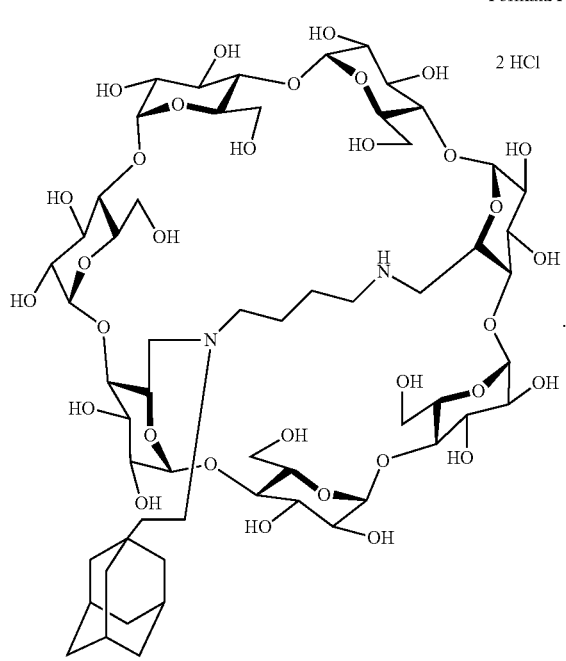

Formula I-1

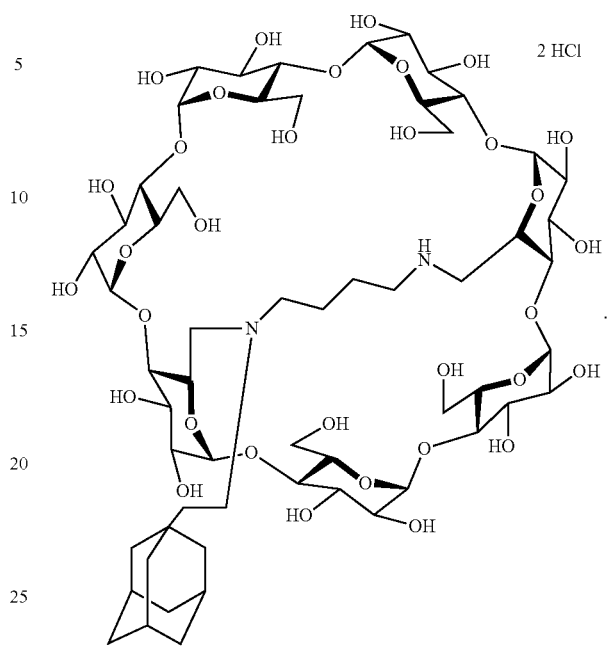

Formula I-1

13. A siRNA-cyclodextrin complex comprising a supramolecular polymer according to claim 11.

14. A method for manufacturing a cyclodextrin-adamantane conjugate according to claim 7 having the following formula I-1:

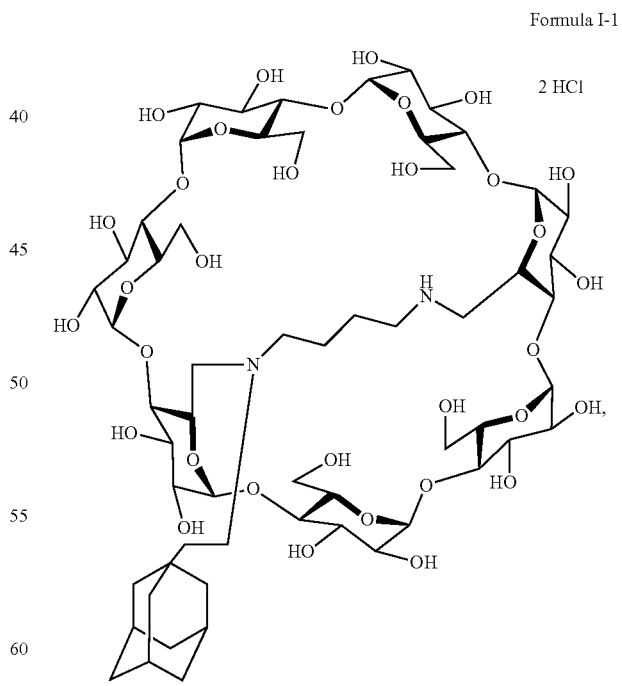

Formula I-1

11. A supramolecular polymer consisting of capped cyclodextrin-hydrophobic moiety conjugates according to claim 1 bridged to each other by inclusion of the hydrophobic moiety of each capped cyclodextrin-hydrophobic moiety conjugate into a cavity of another capped cyclodextrin-hydrophobic moiety conjugate.

12. The supramolecular polymer according to claim 11, wherein the capped cyclodextrin-hydrophobic moiety conjugates have the following formula I-1:

the method comprising the following steps:
a) benzylation of the hydroxyl groups of an α- or β-cyclodextrin, thereby obtaining a perbenzylated α- or βcyclodextrin, b) debenzylation of the benzyl groups in position A and D of the primary rim of the perbenzylated α- or β-cyclodextrin obtained in step a), by regioselective reduction, thereby obtaining a perbenzylated diol α- or β-cyclodextrin, c) oxidation of the hydroxyl groups to aldehyde in position A and D of the primary rim of the perbenzylated diol α- or β-cyclodextrin obtained in step b), by Swern oxidation, thereby obtaining a perbenzylated dialdehyde α- or β-cyclodextrin, d) double reductive amination with putrescine of the compound obtained in step c) thereby obtaining a capped perbenzylated α- or β-cyclodextrin in which the cap has the formula $NH(CH_2)_4NH$, each N atom of which this cap being bound to each of the carbon atoms previously functionalized with an aldehyde group of the compound obtained in step c), e) reductive amination in presence of an adamantane group having a carbonyl functionality, of the capped perbenzylated α- or β-cyclodextrin obtained in step d), thereby obtaining a mixture of:
  a capped perbenzylated α- or β-cyclodextrin which is functionalized with one adamantane group, and
  a capped perbenzylated α- or β-cyclodextrin functionalized with two adamantane groups, f) purification of the mixture of compounds obtained in step e) by chromatography on a silica gel column, thereby obtaining the desired capped perbenzylated α- or β-cyclodextrin-adamantane conjugate functionalized with one adamantane group, g) debenzylation of the perbenzylated cyclodextrin-adamantane conjugate obtained in step f) by catalytic hydrogenation in water/THF in presence of trifluoroacetic acid, thereby obtaining a trifluoroacetate salt of the desired cyclodextrin-adamantane conjugate, and optionally, h) exchange of the trifluoroacetate ions with hydrochloride ions.

15. A method for manufacturing a supramolecular polymer according to claim 11 comprising a step of solubilization of a capped cyclodextrin-hydrophobic moiety conjugates in water or in an aqueous solution, the capped cyclodextrin-hydrophobic moiety conjugate comprising a cyclodextrin moiety and at least one hydrophobic moiety, wherein:
  the cyclodextrin moiety is capped on its primary rim by a cap binding a first carbon atom, previously bearing a hydroxyl group, of a first glucopyranose unit to a second carbon, previously bearing an hydroxyl group, of a second and different glucopyranose unit, said first and second glucopyranose units being preferably separated from each other by at least one, and
  the hydrophobic moiety is bound by a first linker to one of the carbon atoms of the cap, and
  the hydrophobic moiety is selected from the group consisting of an adamantane group, a $C_2$-$C_{13}$ alkyl group optionally containing at least one heteroatom, a $C_5$-$C_6$ aromatic group optionally containing at least one heteroatom, and a $C_3$-$C_8$ non-aromatic cycle optionally containing at least one heteroatom.

16. A method for manufacturing a siRNA-cyclodextrin complex according to claim 13 comprising the following steps:
  a) solubilization of capped cyclodextrin-hydrophobic moiety conjugates according to claim 1 in Dubelcco's Modified Eagle medium (DMEM), Stromal Vascular Fraction (SVF) 10% without antibiotics,
  b) incubation of the solution obtained in step a) during 5 minutes at a temperature comprised between 15° C. and 35° C.,
  c) solubilizing SiRNAs in an Opti-MEM medium SVF,
  d) incubation of the solution obtained in step c) during 5 minutes at a temperature comprised between 15° C. and 35° C., and
  e) mixing the incubated solutions obtained in steps b) and d).

17. The method of claim 15, wherein the capped cyclodextrin-hydrophobic moiety conjugate has one of the following formulae I-1 to I-26:

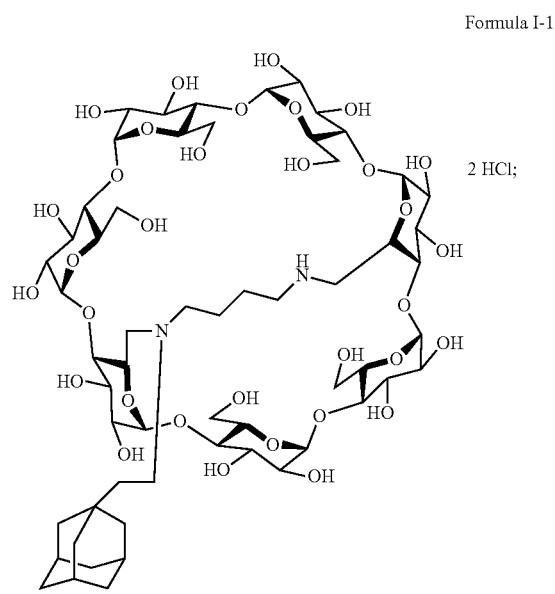

Formula I-1

Formula I-2

Formula I-3

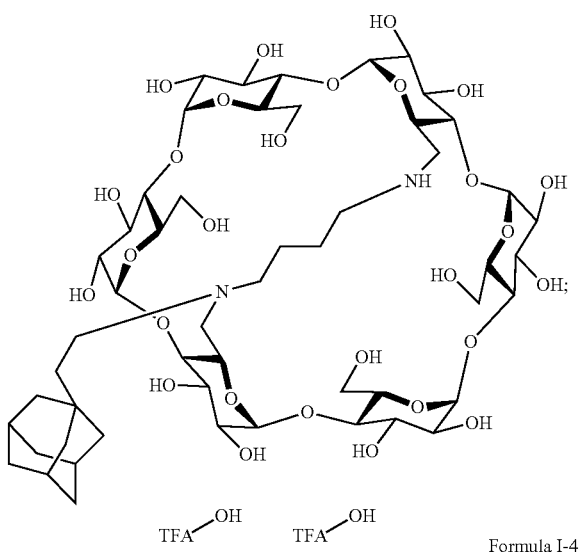

Formula I-4

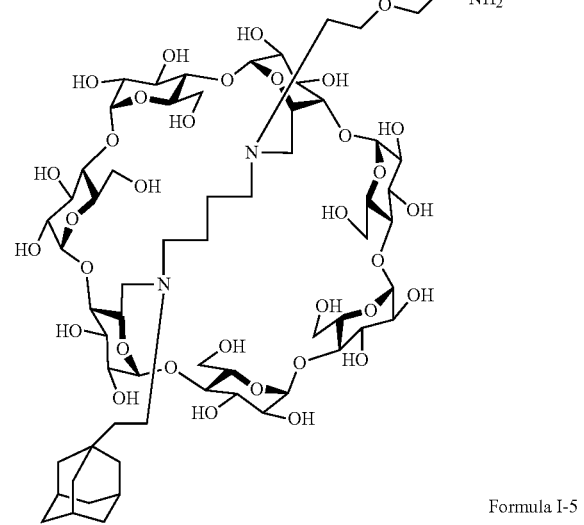

Formula I-5

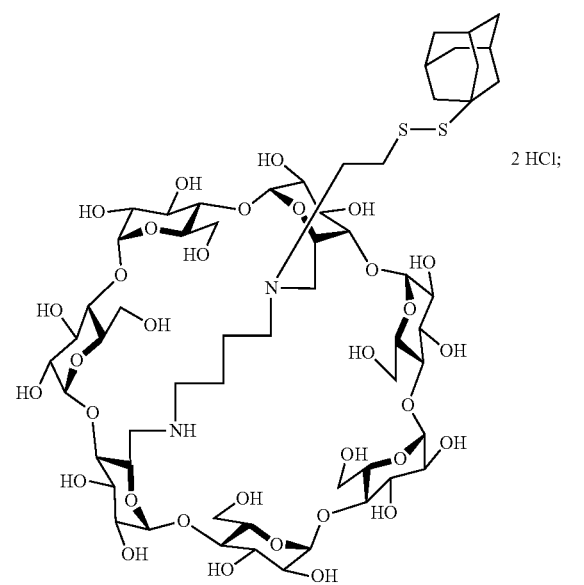

Formula I-6

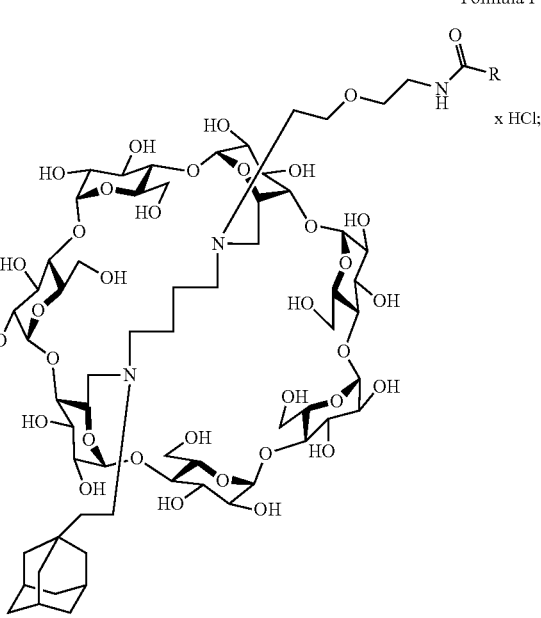

in which R is an amine group, an arginine group, a guanidine group, or a linear or branched chain comprising between 1 and 20 atoms for the main chain, these atoms being nitrogen atoms and/or oxygen atoms and/or carbon atoms, such a chain optionally comprising from 1 to 30 amine groups or guanidine groups, and in which x is equal to the number of amine group(s) plus the number of guanidine group(s) in R;

Formula I-7

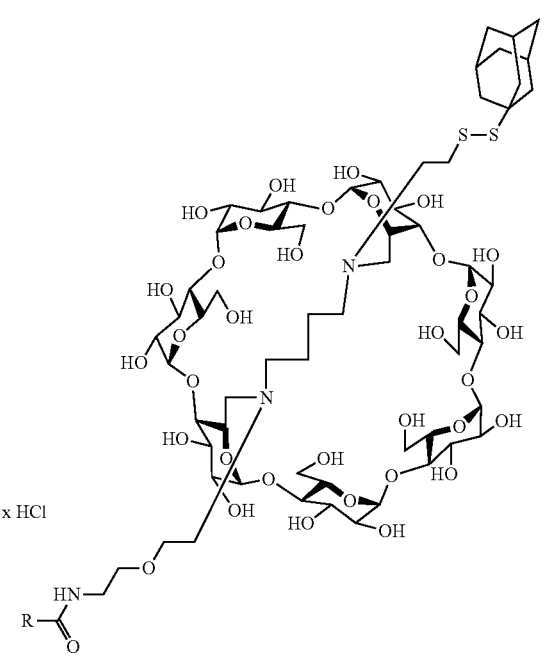

in which R is an amine group, an arginine group, a guanidine group, or a linear or branched chain comprising between 1 and 20 atoms for the main chain, these atoms being nitrogen atoms and/or oxygen atoms and/or carbon atoms, such a chain optionally comprising from 1 to 30 amine groups or guanidine groups, and in which x is equal to the number of amine group(s) plus the number of guanidine group(s) in R;
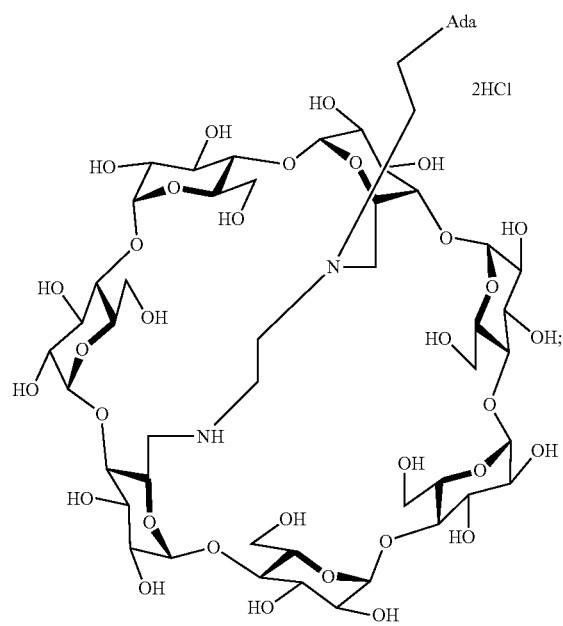
Formula I-8
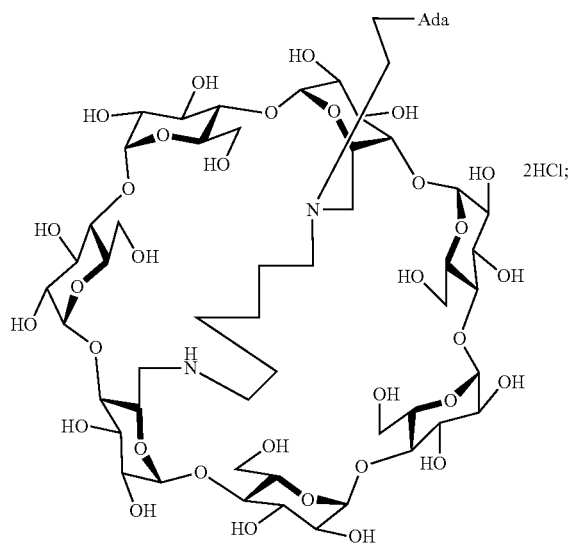
Formula I-9
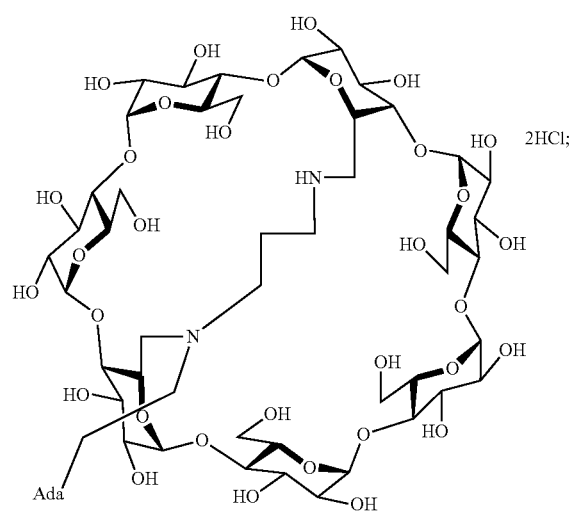
Formula I-10
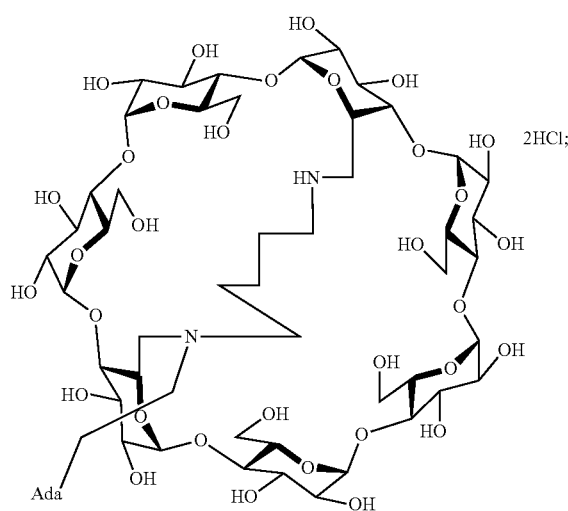
Formula I-11

-continued
Formula I-12
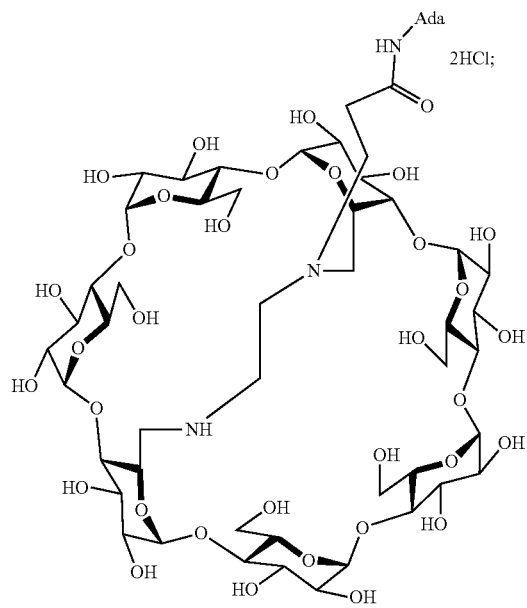
Formula I-13
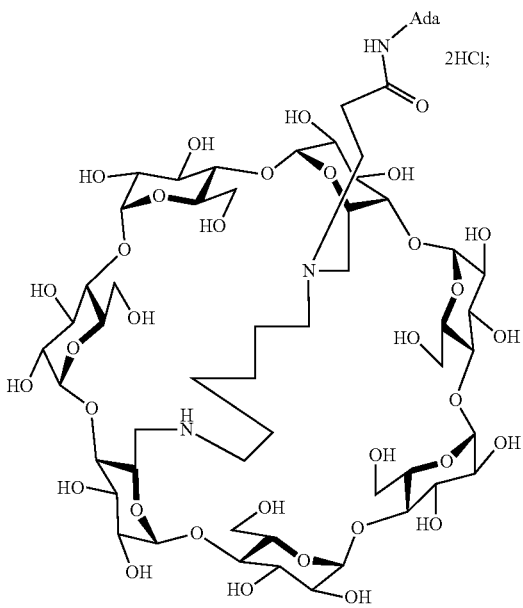
Formula I-14
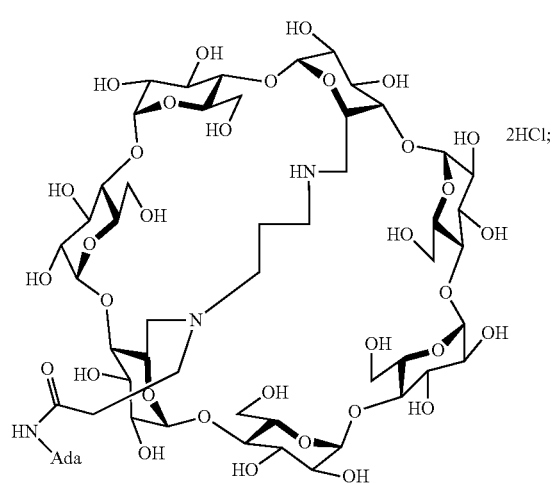
Formula I-15
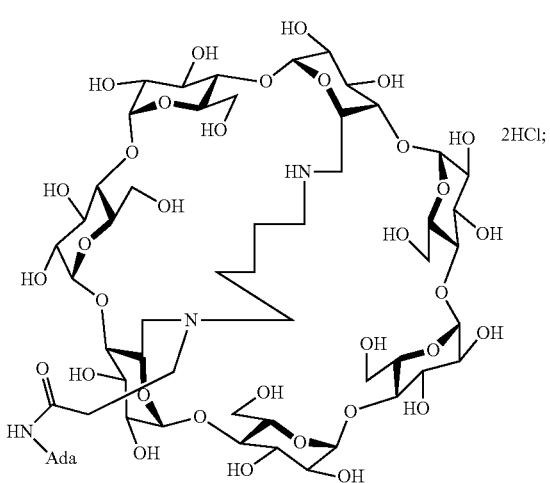
Formula I-16
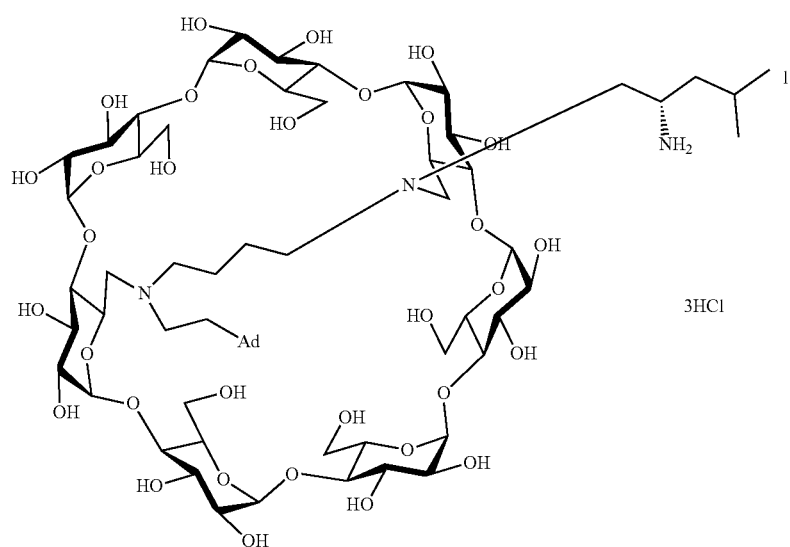

-continued
Formula I-17
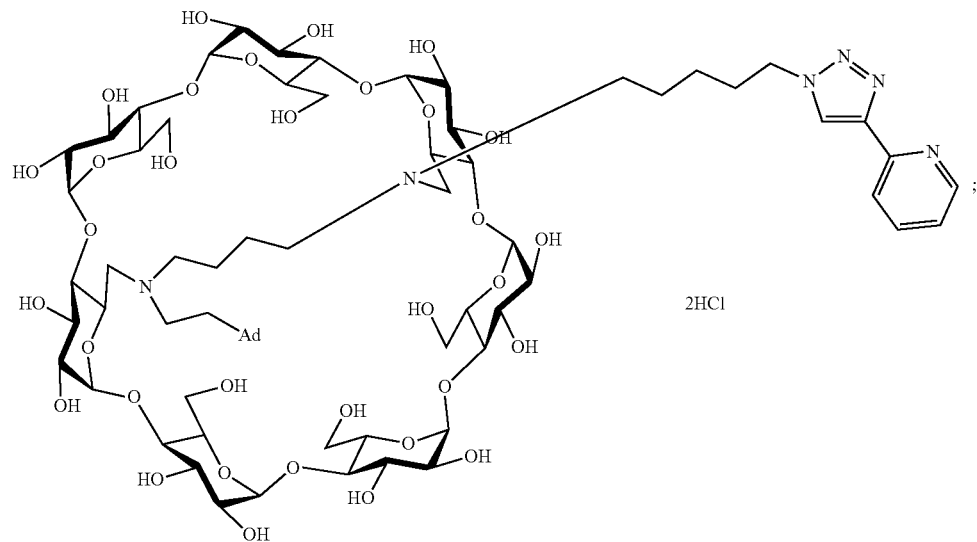
Formula I-18
Formula I-19
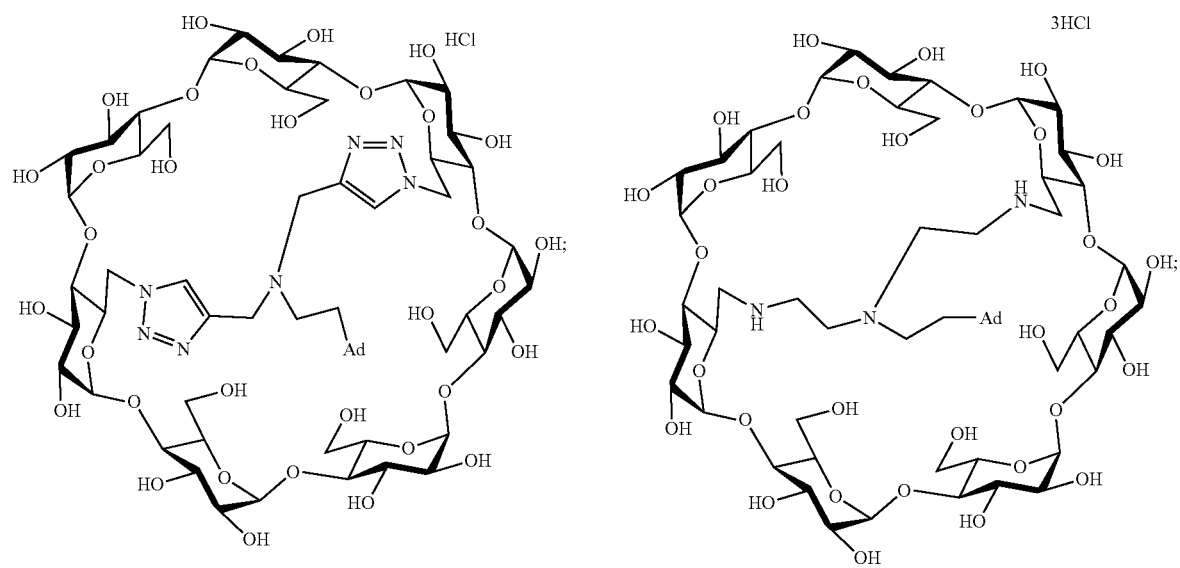
Formula I-20
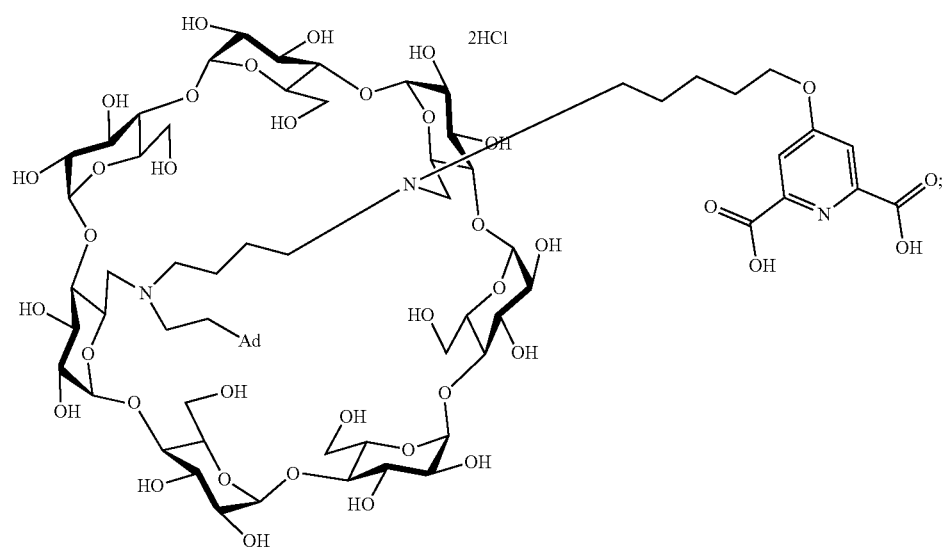

Formula I-21
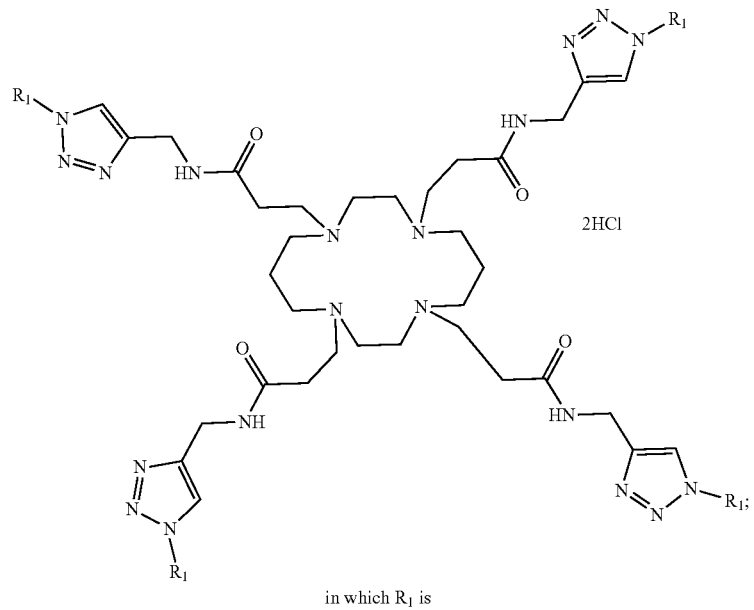
2HCl
in which $R_1$ is
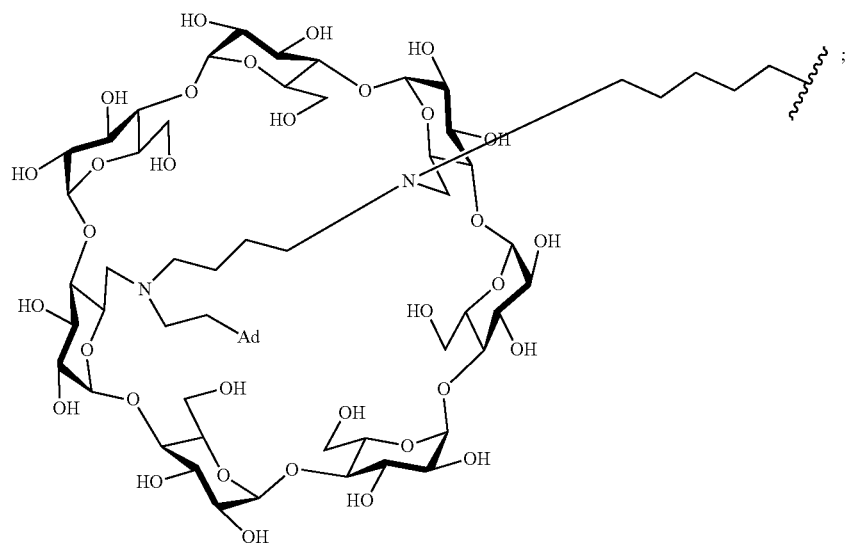

Formula I-22
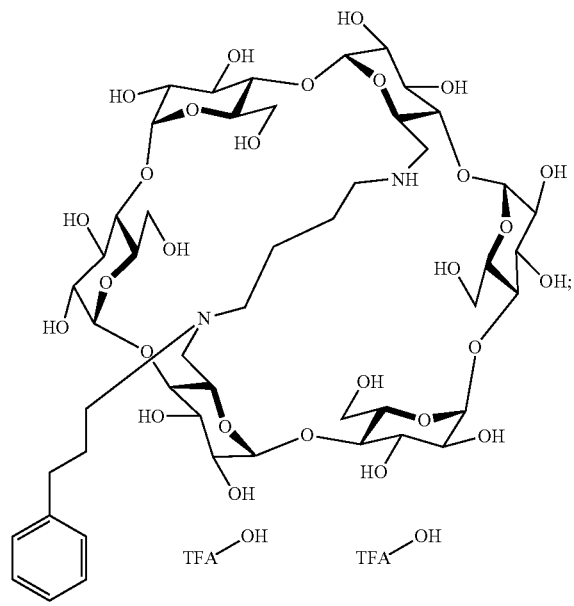
Formula I-23
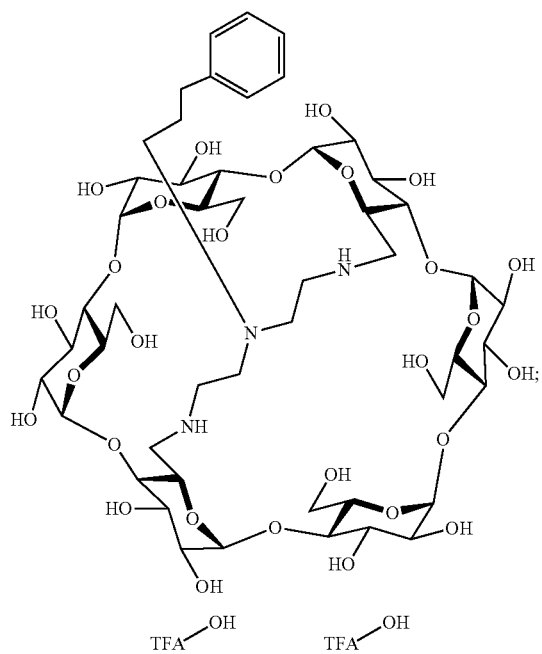
Formula I-24
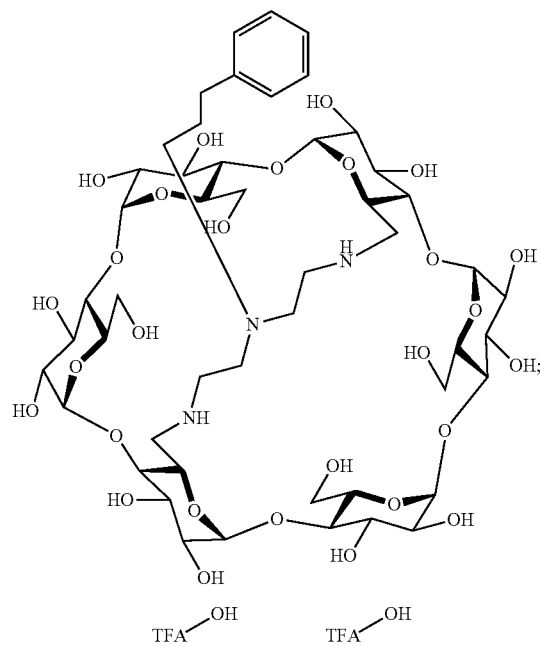

Formula I-25
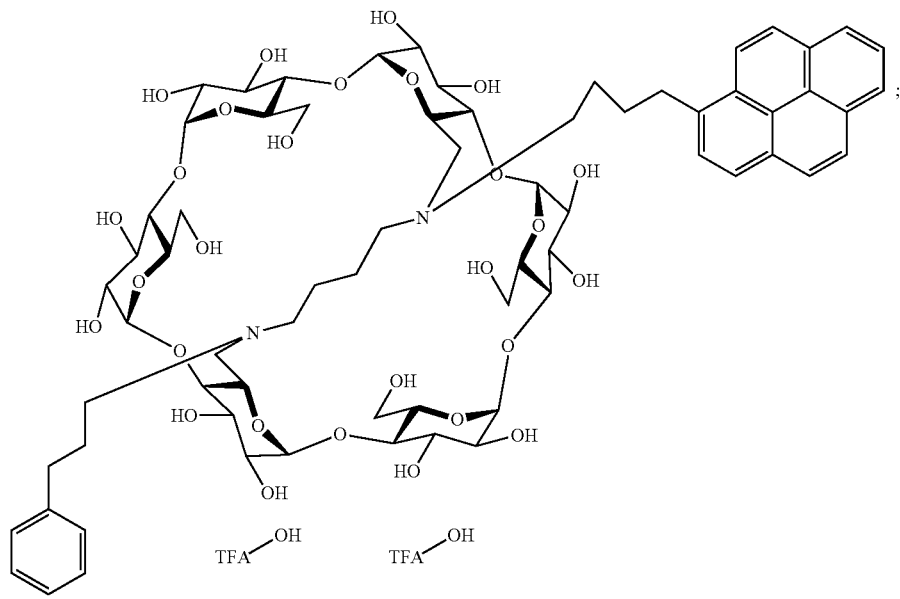
Formula I-26
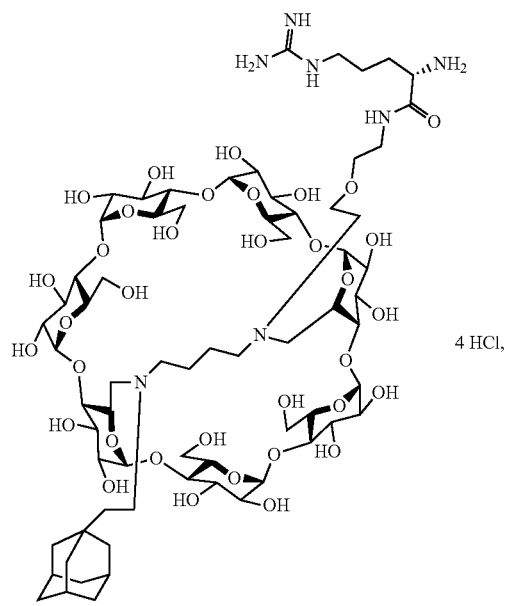

wherein in formulas I-4 to I-11, "Ada" designates an adamantane group and in formulas I-12 to I-17, "Ad" designates an adamantane group.

18. The method of claim 15, wherein the capped cyclodextrin-hydrophobic moiety conjugate has the following formula I-1:

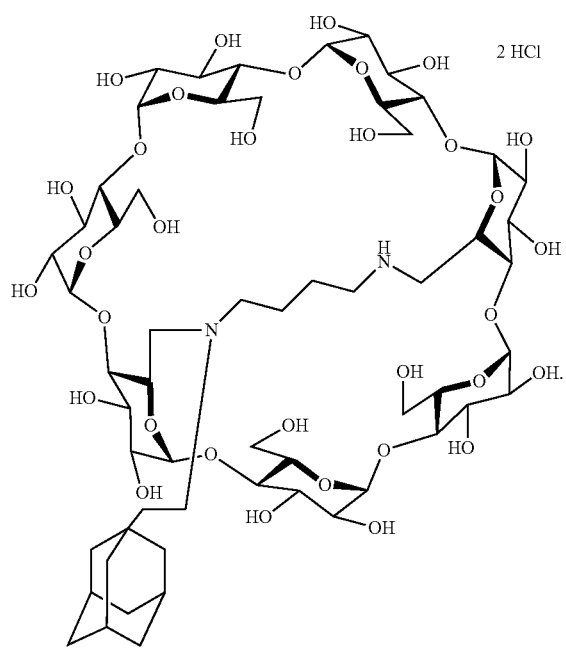

Formula I-1

19. The capped cyclodextrin-hydrophobic moiety conjugate of claim 1, wherein said cap and said first linker, independently from each other, form, together with the carbon atoms to which they are bound, a chain having from 2 to 12 links.

20. The capped cyclodextrin-hydrophobic moiety conjugate according to claim 9, wherein in formulae I-6 and I-7, R is selected from the group consisting of an amine group, an arginine group, a guanidine group, and one of the following groups:

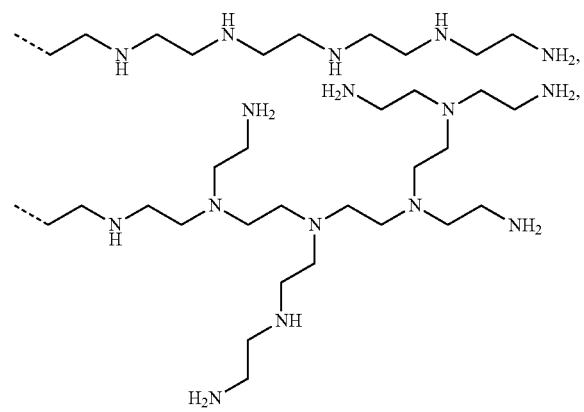

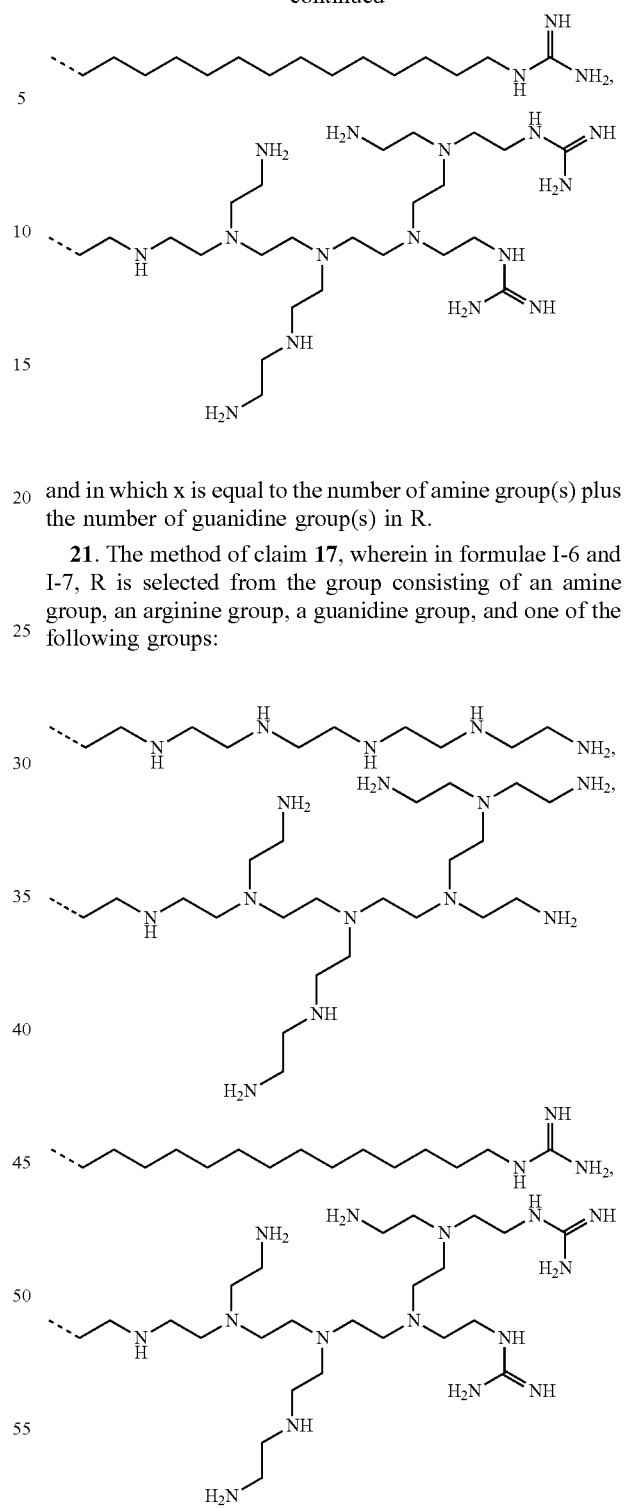

and in which x is equal to the number of amine group(s) plus the number of guanidine group(s) in R.

21. The method of claim 17, wherein in formulae I-6 and I-7, R is selected from the group consisting of an amine group, an arginine group, a guanidine group, and one of the following groups:

and in which x is equal to the number of amine group(s) plus the number of guanidine group(s) in R.

* * * * *

UNITED STATES PATENT AND TRADEMARK OFFICE
CERTIFICATE OF CORRECTION

PATENT NO. : 10,947,323 B2
APPLICATION NO. : 16/329423
DATED : March 16, 2021
INVENTOR(S) : Sollogoub et al.

It is certified that error appears in the above-identified patent and that said Letters Patent is hereby corrected as shown below:

In the Claims

Column 39,
Line 27, "non: aromatic" should read --non-aromatic--.

Column 43,
In Formula I-8, insert --2HC1-- above "Ada".

Column 53,
In Formula I-26, remove numeral "5" from formula.

Column 63 and 64,
In Formula I-16, in the upper right area, "1" should read --;--.

Signed and Sealed this
Thirteenth Day of September, 2022

Katherine Kelly Vidal
*Director of the United States Patent and Trademark Office*